United States Patent
Kan et al.

(10) Patent No.: US 9,848,756 B2
(45) Date of Patent: *Dec. 26, 2017

(54) COMPACT MONITOR STAND

(71) Applicant: EndoChoice, Inc., Alpharetta, GA (US)

(72) Inventors: Gil Kan, Alpharetta, GA (US); Charlie Jacobs, Loganville, GA (US); Mark Gilreath, Alpharetta, GA (US); Will Parks, Lawrenceville, GA (US); Gregg Costantino, Medford, NJ (US); Eddie Cochrane, Ramsey, NJ (US); George Cronin, Wilmington, MA (US)

(73) Assignee: EndoChoice, Inc., Alpharetta, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/949,153

(22) Filed: Nov. 23, 2015

(65) Prior Publication Data

US 2016/0183768 A1    Jun. 30, 2016

Related U.S. Application Data

(63) Continuation of application No. 14/594,947, filed on Jan. 12, 2015, now Pat. No. 9,247,861.
(Continued)

(51) Int. Cl.
*A61B 1/04* (2006.01)
*H04N 5/655* (2006.01)
(Continued)

(52) U.S. Cl.
CPC ....... *A61B 1/00048* (2013.01); *F16M 11/046* (2013.01); *F16M 11/105* (2013.01);
(Continued)

(58) Field of Classification Search
CPC ......... H04N 5/64; H04N 5/645; H04N 5/655; A61B 1/00048; F16M 11/045;
(Continued)

(56) References Cited

U.S. PATENT DOCUMENTS 5,687,939 A    11/1997  Moscovitch
6,189,849 B1    2/2001  Sweere
(Continued)

OTHER PUBLICATIONS

Notice of Allowance dated Sep. 15, 2015 for U.S. Appl. No. 14/594,947.

*Primary Examiner* — Michael Safavi
(74) *Attorney, Agent, or Firm* — Bookoff McAndrews, PLLC

(57) ABSTRACT

The present specification provides an apparatus for supporting one or more monitors. The apparatus includes a base stand having one or more wheels for enabling movement of the apparatus; a first rigid frame having a top end and a bottom end attached with the base stand; a second extendable frame having a top end and a bottom end and telescopically movable within the first rigid frame; a monitor arm assembly removably coupled with the top end of the second frame and configured to receive a plurality of monitors. The apparatus is transformable from a first collapsed configuration for transport and storage into a second operational configuration by rotating or removing the monitor arm assembly and by moving the second extendable frame relative to the first rigid frame.

20 Claims, 15 Drawing Sheets

Related U.S. Application Data

(60) Provisional application No. 61/939,566, filed on Feb. 13, 2014, provisional application No. 61/926,769, filed on Jan. 13, 2014.

(51) Int. Cl.
 *F16M 11/28* (2006.01)
 *A61B 1/00* (2006.01)
 *F16M 11/42* (2006.01)
 *F16M 11/04* (2006.01)
 *F16M 11/10* (2006.01)

(52) U.S. Cl.
 CPC ............. *F16M 11/28* (2013.01); *F16M 11/42* (2013.01); *H04N 5/655* (2013.01); *Y10T 29/49716* (2015.01)

(58) Field of Classification Search
 CPC .... F16M 11/046; F16M 11/105; F16M 11/28; F16M 11/42
 USPC .................. 348/836, 838, 840; 345/1.1, 1.3; 248/121, 122.1, 125.1, 125.8, 125.9, 126, 248/218.4, 201, 309.1, 274.1, 917
 See application file for complete search history.

(56) References Cited

U.S. PATENT DOCUMENTS

| | | |
|---|---|---|
| 6,783,105 B2 | 8/2004 | Oddsen, Jr. |
| 6,938,869 B2 | 9/2005 | Lin |
| 7,389,963 B2 | 6/2008 | Cho |
| 7,530,538 B2 | 5/2009 | Whalen |
| 8,191,487 B2 | 6/2012 | Theesfeld |
| 8,342,462 B2 | 1/2013 | Sapper |
| 8,523,131 B2 | 9/2013 | Derry |
| 8,567,735 B2 | 10/2013 | Burgess |
| 8,833,716 B2 | 9/2014 | Funk |
| 8,839,723 B2 | 9/2014 | Hazzard |
| 8,967,560 B2 | 3/2015 | Ergun |
| 9,080,721 B2 | 7/2015 | Hazzard |
| 2004/0188573 A1 | 9/2004 | Weatherly |
| 2006/0096505 A1 | 5/2006 | Sykes |
| 2007/0084978 A1 | 4/2007 | Martin |
| 2007/0145203 A1 | 6/2007 | Takada |
| 2009/0173847 A1 | 7/2009 | Dittmer |
| 2012/0056050 A1 | 3/2012 | Huang |
| 2012/0119040 A1 | 5/2012 | Ergun |
| 2012/0187056 A1 | 7/2012 | Hazzard |
| 2014/0245932 A1 | 9/2014 | McKenzie |
| 2015/0198280 A1 | 7/2015 | Ergun |

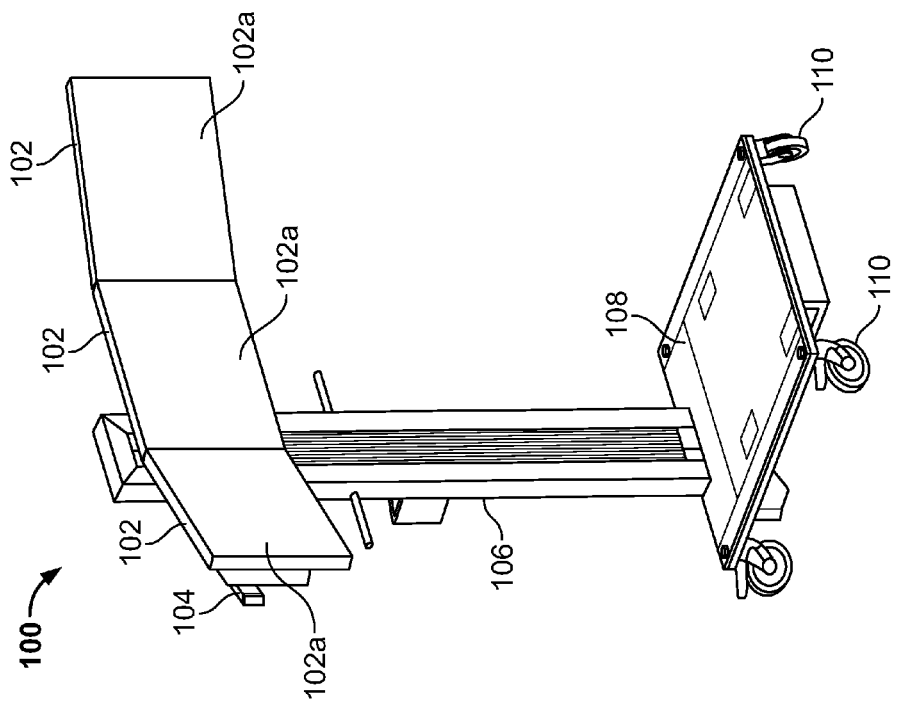
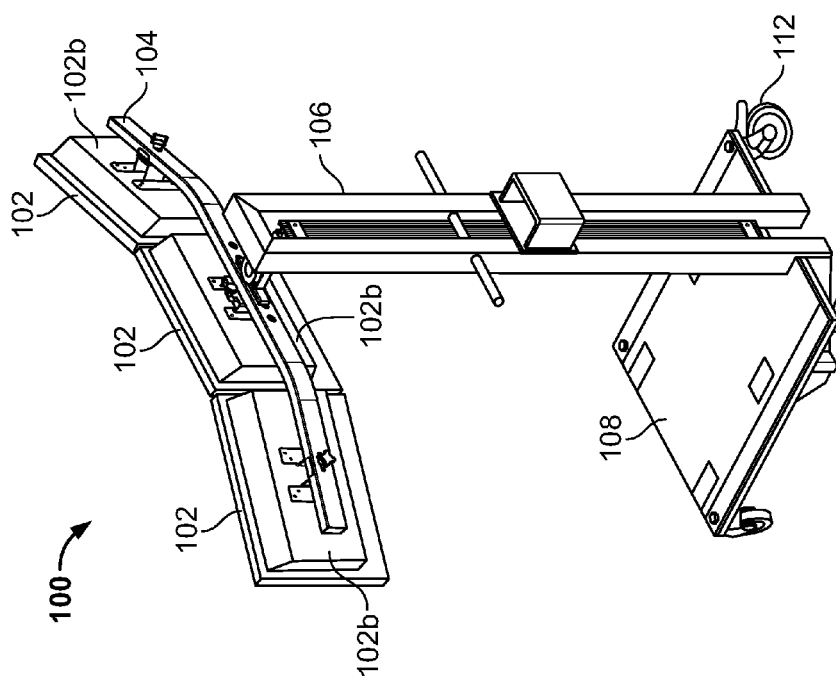

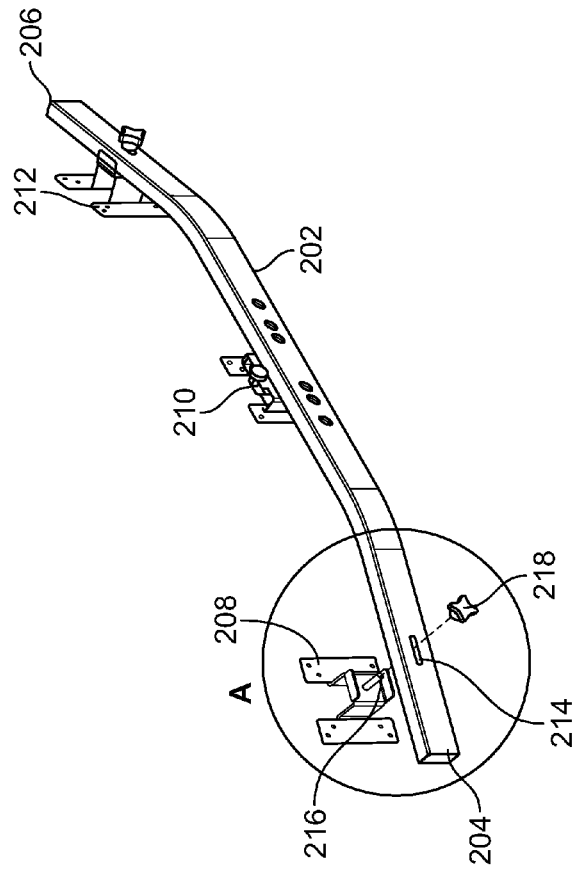
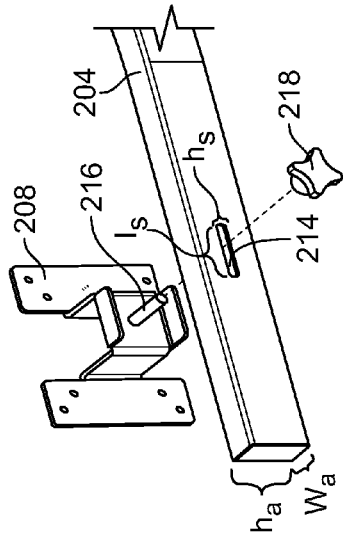
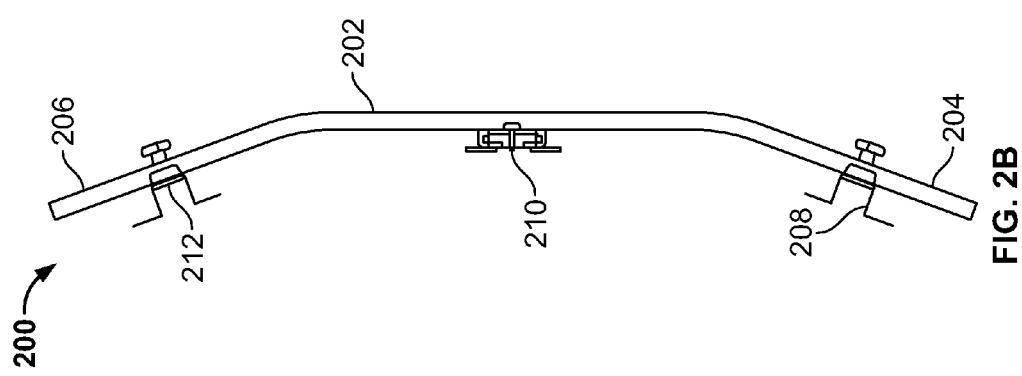
FIG. 2C
FIG. 2D
FIG. 2B

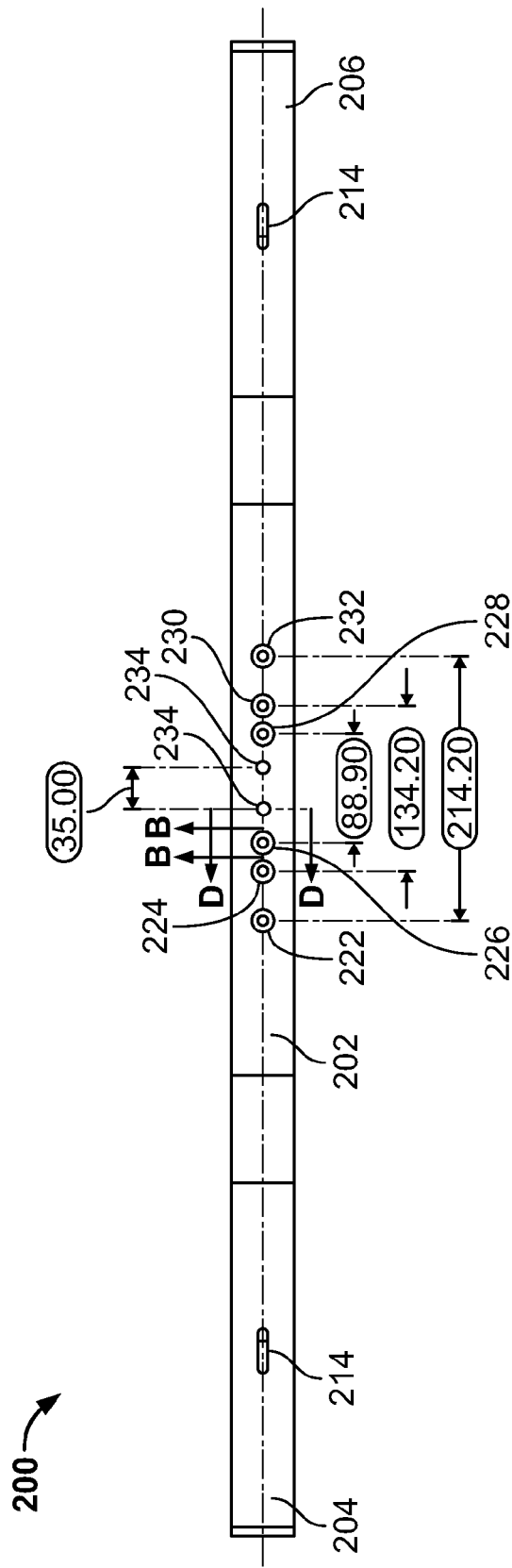

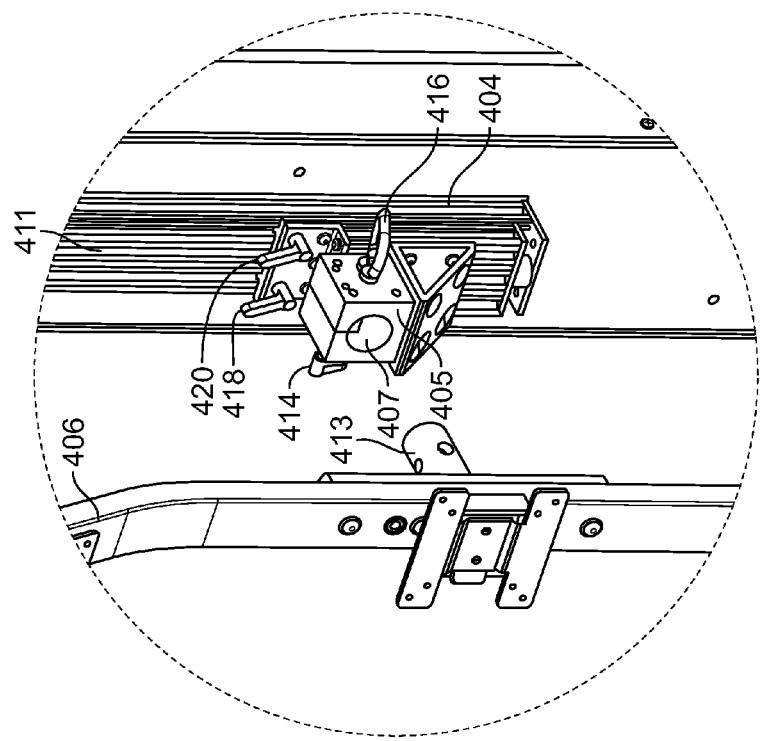
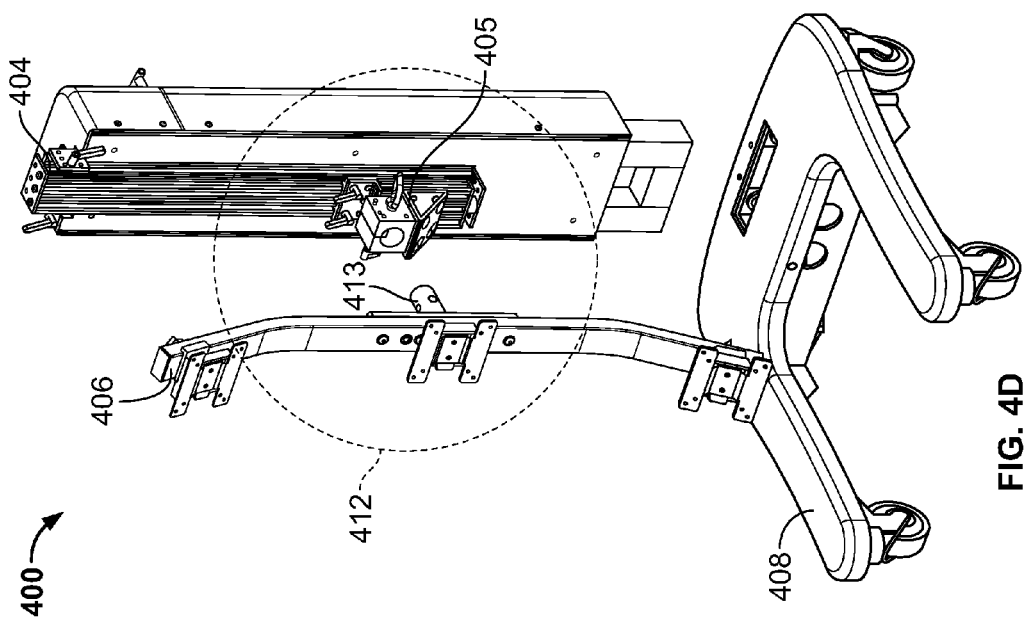
FIG. 4E
FIG. 4D

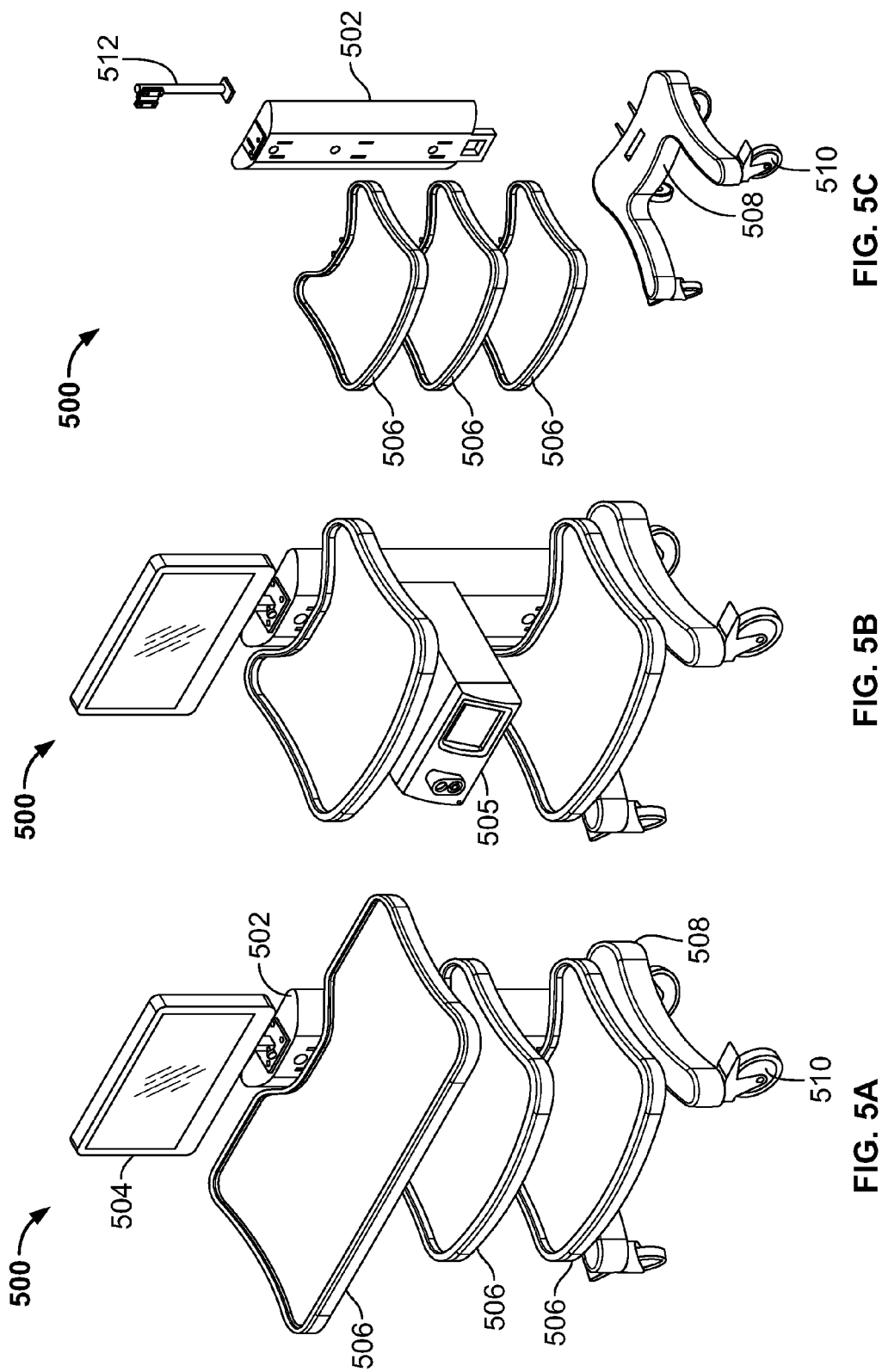

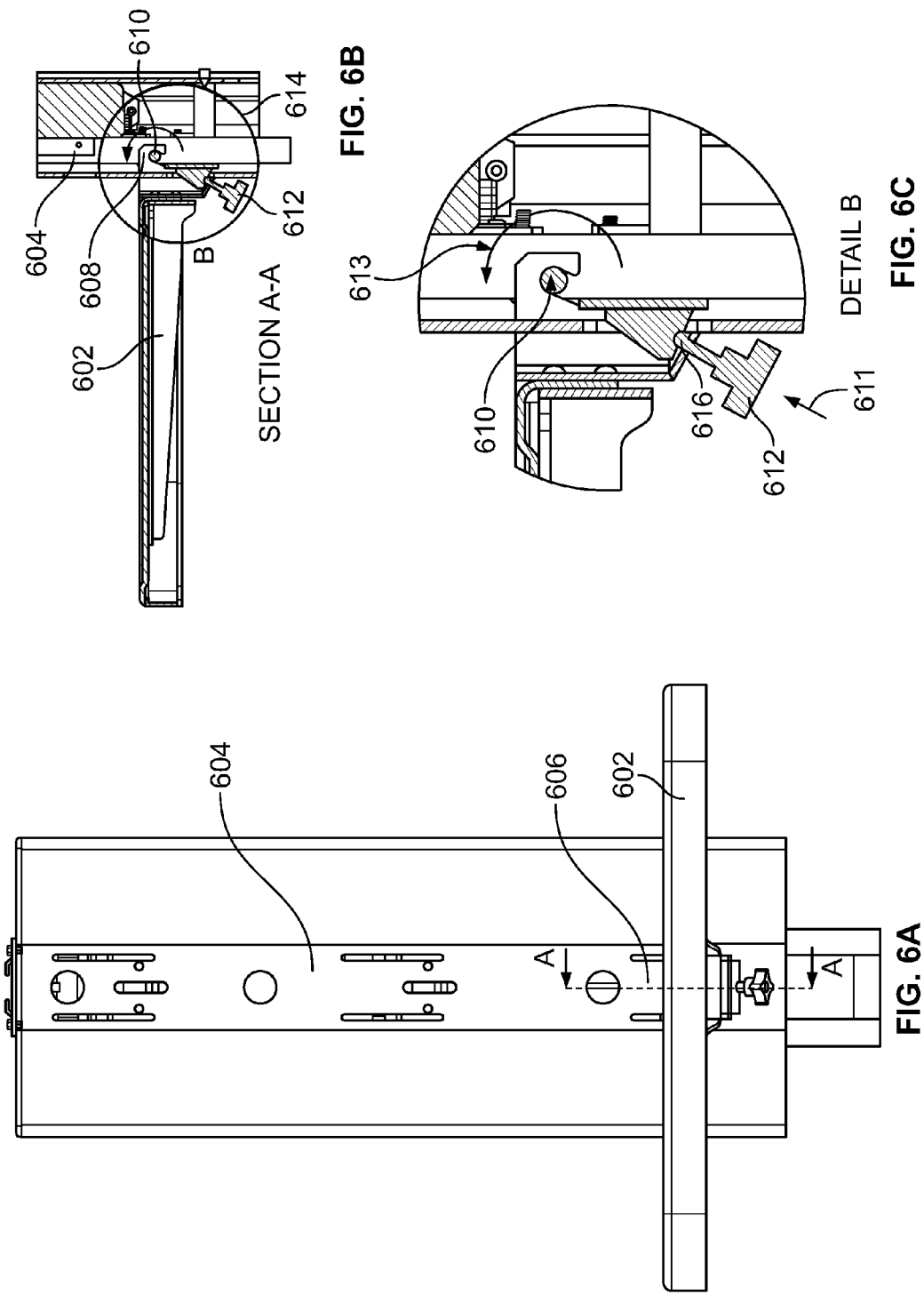

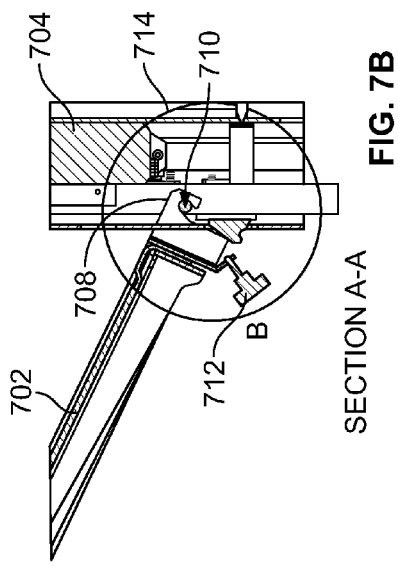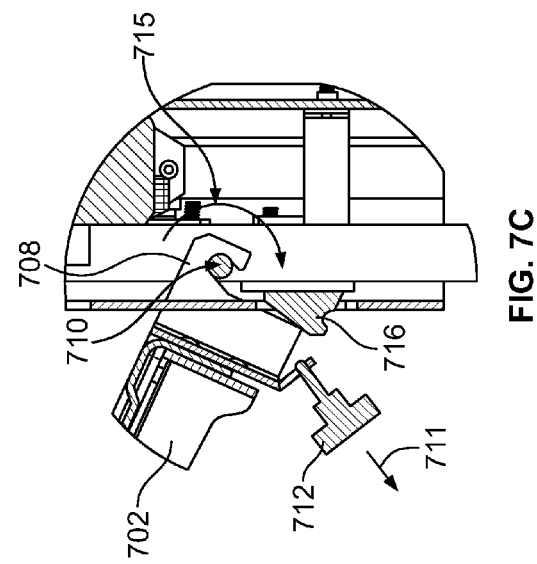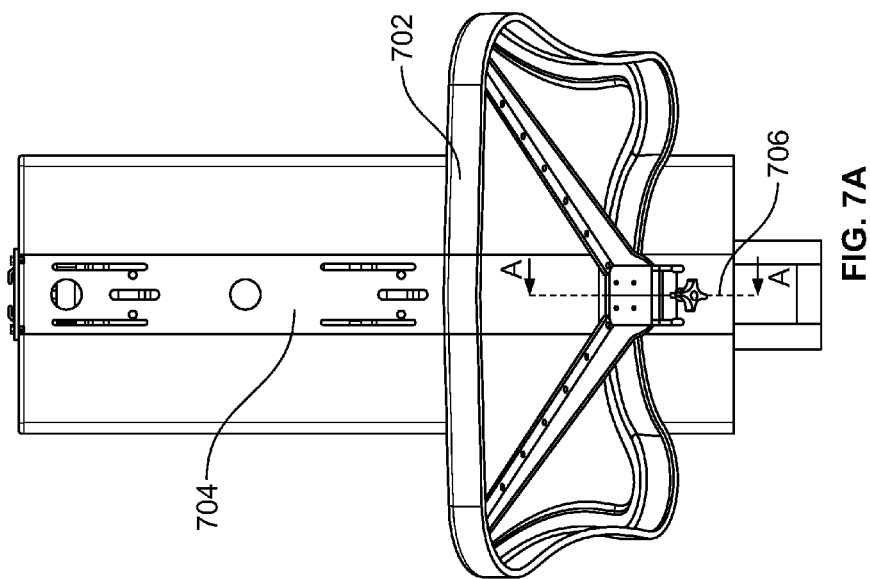

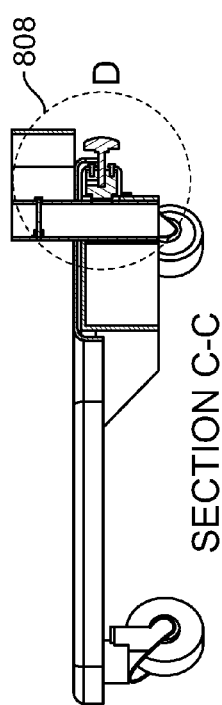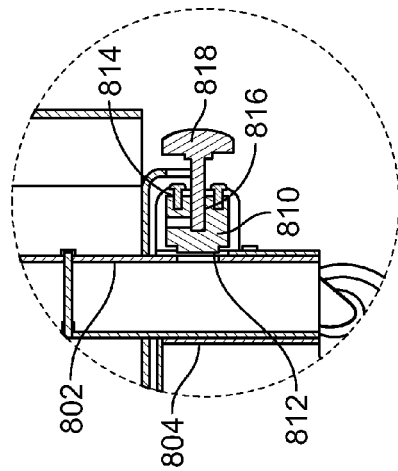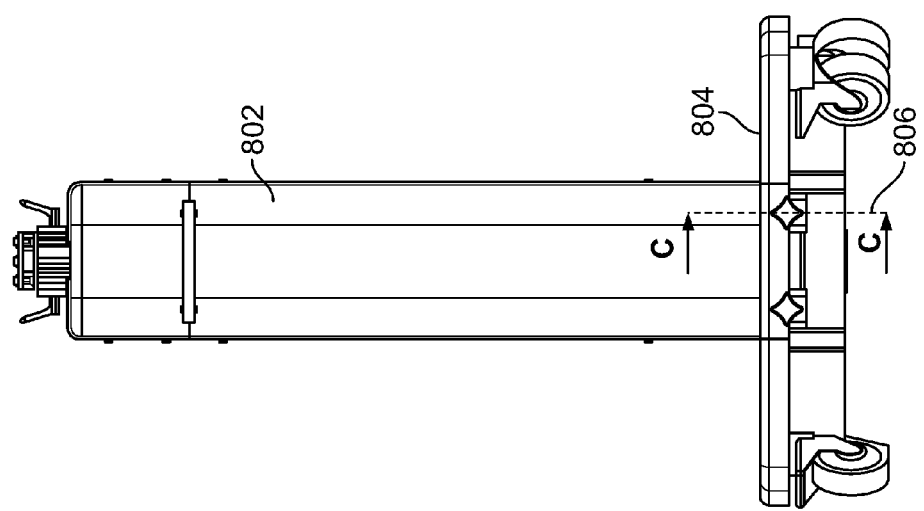

COMPACT MONITOR STAND

CROSS-REFERENCE TO RELATED APPLICATIONS

The present application is a continuation application of U.S. patent application Ser. No. 14/594,947, entitled "Compact Monitor Stand" and filed on Jan. 12, 2015, which relies upon, for priority, U.S. Provisional Patent Application No. 61/926,769, entitled "Monitor Stand" and filed on Jan. 13, 2014, and U.S. Provisional Patent Application No. 61/939,566, entitled "Compact Monitor Stand" and filed on Feb. 13, 2014.

U.S. patent application Ser. No. 14/594,947 is also related to U.S. patent application Ser. No. 14/273,923, entitled "Operational Interface In A Multi-Viewing Elements Endoscope", and filed on May 9, 2014, which relies upon U.S. Provisional Patent Application No. 61/822,563, entitled "Systems and Methods for Displaying a Plurality of Contiguous Images with Minimal Distortion" and filed on May 13, 2013.

All of the above-mentioned applications are herein incorporated by reference in their entirety.

FIELD

The present specification relates generally to endoscopes, and more specifically, to a stand for supporting one or more endoscope monitor screens. The present specification also relates to a monitor stand cart that can be used to carry endoscopic equipment and may be transported in a medium sized vehicle.

BACKGROUND

An endoscope conventionally comprises an elongated tubular shaft, rigid or flexible, having a video camera and/or a fiber optic lens assembly at its distal end. Various surgical tools may be inserted through a working channel in the endoscope for performing different surgical procedures. Endoscopes, such as colonoscopes, that are currently being used, typically have a front camera for viewing the internal organ, such as the colon, an illuminator, a fluid injector for cleaning the camera lens, and a working channel for insertion of surgical tools, for example, for removing polyps found in the colon. Often, endoscopes also have fluid injectors ("jet") for cleaning a body cavity, such as the colon, into which they are inserted. The illuminators commonly used are fiber optics which transmit light, generated remotely, to the endoscope tip section.

Endoscopes having multiple viewing elements, such as cameras, generate multiple video feeds which require display. These video feeds are typically generated in native or standard square formats of aspect ratios 4:3 or 5:4. Such native square formatted video feeds when displayed on widescreen or rectangular monitors cause 'pillar-boxing' if not modulated to fit the widescreen but result in unacceptable image/video distortion if modulated to fill the entire widescreen.

Hence, the video feeds generated by a plurality of viewing elements of an endoscopic tip are processed such that the video feeds can be displayed appropriately on a plurality of advantageous configurations of widescreen monitors. Usually three monitors (a left, a center and a right side monitor) are placed side-by-side or contiguously. In some cases, the three monitors together provide a panoramic view based on an overlap between fields of view of the three viewing elements (front-looking and the two side-looking viewing elements).

There is need for an arrangement for supporting the monitors so that they may be viewed by an operating physician with ease.

SUMMARY

The present specification discloses an apparatus for supporting one or more monitors, comprising: a base stand comprising one or more wheels; a rigid frame stand having a top end and a bottom end coupled with the base stand and comprising a center frame portion extending from said top end to said bottom end; a pivoting mechanism comprising: a pivoting bracket attached to and vertically slidable along said center frame portion; a pivoting post fixedly attached to said pivoting bracket; and a pivoting bearing positioned on and horizontally rotatable about said pivoting post; a monitor arm assembly having a bow shape with a concave surface, a convex surface, a center portion, left end portion, right end portion and a center bracket attached to said center portion wherein the concave surface of each of said portions is configured to fixedly receive a monitor, further wherein said center bracket attaches to said pivoting bearing on said convex surface; wherein said monitor arm assembly is horizontally rotatable relative to said rigid frame stand by rotating said pivoting bearing about said pivoting post and a height of said monitor arm assembly is adjustable by sliding said pivoting bracket along said center frame portion.

Optionally, the apparatus further comprises a locking mechanism for locking said pivoting bracket at a fixed vertical position on said center frame portion.

The apparatus may be configured to receive a left monitor, a center monitor, and a right monitor such that a right edge of said left monitor is flush with a left edge of said center monitor and a left edge of said right monitor is flush with a right edge of said center monitor.

Optionally, said left portion and said right portion of said monitor arm assembly each include a slot configured to receive a bracket for attaching a monitor wherein said bracket is horizontally slidable within said slot for adjusting a horizontal position of an attached monitor. Each slot may be positioned approximately 120.0 millimeters to 140.0 millimeters, and more preferably 130.9 millimeters, from a free end of said left portion and said right portion opposite said center portion. Each slot may have a length ranging from approximately 25.0 millimeters to 50.0 millimeters, and more preferably 38.2 millimeters. Optionally, each bracket includes a flange on a top and bottom edge of said bracket to prevent rotational movement of the bracket about said monitor arm assembly.

Each of said left and right portions of said monitor arm assembly may be bent at angle of approximately 20 degrees with respect to a horizontal plane of said center portion to create said bow shape.

Optionally, the base stand is an isolation transformer assembly stand for supporting an isolation transformer, the isolation transformer assembly stand balancing the weight of the monitors coupled with the monitor arm assembly.

Optionally, an underside of the isolation transformer assembly stand is coupled with two front wheels and two rear wheels enabling movement of the assembly stand, wherein at least the rear wheels comprise a locking mechanism for fixing position of the apparatus.

Optionally, said monitor arm assembly is hollow, composed of aluminum, and includes a plurality of spacers configured to provide structural strength to said monitor arm assembly.

The present specification also discloses an apparatus for supporting one or more monitors, comprising: a base stand comprising one or more wheels; a first rigid frame portion having a top end and a bottom end coupled with the base stand; a second extendable frame portion having a top end, a bottom end, and a channel extending from said top end to said bottom end, said second extendable frame portion being telescopically extendable from and into said top of said first rigid frame portion from a first top vertical position to a second bottom vertical position and a plurality of vertical positions therebetween; a locking mechanism for fixing said second extendable frame portion in a vertical position within said first rigid frame portion; a coupling component having at least one opening, a first plurality of holes, and a second plurality of holes and positioned and vertically slidable within said channel from a third top vertical position to a fourth bottom vertical position and a plurality of vertical positions therebetween; a monitor arm assembly having a bow shape with a concave surface, a convex surface, a center portion, left end portion, right end portion and a peg extending from said convex surface of said center portion wherein the concave surface of each of said portions is configured to fixedly receive a monitor, and said peg is configured to insert into said at least one opening such that said monitor arm assembly is removably attachable to and rotatable within said coupling component; a first plurality of pins configured to pass through said first plurality of holes in said coupling component and into said peg of said monitor arm assembly to fixedly attach said monitor arm assembly to said coupling component; and a second set of pins configured to pass through said second plurality of holes in said coupling component and into said channel of said second extendable frame portion to lock said coupling component in a vertical position within said channel; wherein said apparatus is transformable from a first collapsed configuration for storage and transport into a second operational configuration for receiving at least one monitor.

The apparatus may be configured to receive a left monitor, a center monitor, and a right monitor such that a right edge of said left monitor is flush with a left edge of said center monitor and a left edge of said right monitor is flush with a right edge of said center monitor.

Optionally, said left portion and said right portion of said monitor arm assembly each include a slot configured to receive a bracket for attaching a monitor wherein said bracket is horizontally slidable within said slot for adjusting a horizontal position of an attached monitor. Each slot may be positioned approximately 120.0 millimeters to 140.0 millimeters, and more preferably 130.9 millimeters, from a free end of said left portion and said right portion opposite said center portion. Each slot may have a length ranging from approximately 25.0 millimeters to 50.0 millimeters, and more preferably 38.2 millimeters. Optionally, each bracket includes a flange on a top and bottom edge of said bracket to prevent rotational movement of the bracket about said monitor arm assembly.

Each of said left and right portions of said monitor arm assembly may be bent at angle of approximately 20 degrees with respect to a horizontal plane of said center portion to create said bow shape.

The locking mechanism may comprise a lever or button which, when actuated, allows said second extendable frame portion to be moved relative to said first rigid frame portion.

Optionally, when in said first collapsed configuration, said second extendable frame portion is in said second bottom vertical position, said coupling component is in said fourth bottom vertical position, and said monitor arm assembly is removed from said coupling component or rotated within said opening of said coupling component such that a long axis of said monitor arm assembly is parallel to said second extendable frame portion.

The apparatus, when in said first collapsed configuration, may have a height of approximately 45.3 inches.

Optionally, when in said second operational configuration, said second extendable frame portion is in said first top vertical position or any vertical position above said second bottom vertical position, said coupling component is in said third top vertical position or any vertical position above said fourth bottom vertical position, and said monitor arm assembly is rotated within said opening of said coupling component such that a long axis of said monitor arm assembly is perpendicular to said second extendable frame portion.

The apparatus, when in said second operational configuration, may have a height of approximately 62.1 inches.

Optionally, the base stand is an isolation transformer assembly stand for supporting an isolation transformer, the isolation transformer assembly stand balancing the weight of the monitors coupled with the monitor arm assembly.

Optionally, an underside of the isolation transformer assembly stand is coupled with two front wheels and two rear wheels enabling movement of the assembly stand, wherein at least the rear wheels comprise a locking mechanism for fixing position of the apparatus.

Optionally, said monitor arm assembly is hollow, composed of aluminum, and includes a plurality of spacers configured to provide structural strength to said monitor arm assembly.

Optionally, said first rigid frame portion is detachable from said base stand.

The base stand, first rigid frame portion with second extendable frame and coupling component, and said monitor arm assembly may have weights of approximately 20 pounds, 35 pounds, and 12 pounds, respectively.

The present specification also discloses a method of transforming a monitor stand from a first collapsed configuration into a second operation configuration, said method comprising the steps of: providing a monitor stand comprising: a base stand comprising one or more wheels; a first rigid frame portion having a top end and a bottom end coupled with the base stand; a second extendable frame portion having a top end, a bottom end, and a channel extending from said top end to said bottom end, said second extendable frame portion being telescopically extendable from and into said top of said first rigid frame portion from a first top vertical position to a second bottom vertical position and a plurality of vertical positions therebetween; a locking mechanism for fixing said second extendable frame portion in a vertical position within said first rigid frame portion; a coupling component having at least one opening, a first plurality of holes, and a second plurality of holes and positioned and vertically slidable within said channel from a third top vertical position to a fourth bottom vertical position and a plurality of vertical positions therebetween; a monitor arm assembly having a bow shape with a concave surface, a convex surface, a center portion, left end portion, right end portion and a peg extending from said convex surface of said center portion wherein the concave surface of each of said portions is configured to fixedly receive a monitor, and said peg is configured to insert into said at least one opening such that said monitor arm assembly is removably attachable to and rotatable within said coupling component; a first plurality of pins configured to pass through said first plurality of holes in said coupling component and into said peg of said monitor arm assembly to fixedly attach said monitor arm assembly to said coupling component; and a second set of pins configured to pass through said second plurality of holes in said coupling component and into said channel of said second extendable frame portion to lock said coupling component in a vertical position within said channel; removing said second plurality of pins; sliding the coupling component to the third top position or any other vertical position above said fourth bottom vertical position; re-inserting said second plurality of pins; releasing said locking mechanism; extending said second extendable frame portion from said top end of said first rigid frame portion to said first top vertical position or any other vertical position above said second bottom position; re-engaging said locking mechanism; removing said first plurality of pins; rotating the monitor arm assembly into a horizontal position perpendicular to said second extendable frame portion; and re-inserting said first plurality of pins.

Optionally, when in said collapsed configuration, said monitor arm assembly is detached from said coupling component, and said method further comprises the initial steps of: removing said second plurality of pins; inserting said peg of said monitor arm assembly into said at least one opening in said coupling component with the monitor arm assembly in a vertical position parallel to said second extendable frame portion; and re-inserting said second plurality of pins.

Optionally, when in said collapsed configuration, said first rigid frame is detached from said base stand, and said method further comprises the initial step of coupling said bottom end of said first rigid frame with said base stand.

The present specification also discloses an apparatus for supporting a monitor and one or more shelves, comprising: a base stand comprising one or more wheels; a rigid spine portion having at least two spacers, a bracket nose surface, a top end and a bottom end coupled with the base stand; a monitor support member coupled to said top end of said spine portion; and at least one shelf removably coupled to said spine portion and comprising a flat surface with two hooked shaped extensions and a knob; wherein linear force applied to said knob in a direction toward said bracket nose surface is converted to rotational torque to cause said hooked shaped extensions to engage said spacers and fixedly secure said shelf to said spine portion.

Optionally, the apparatus further comprises a support shelf for supporting a main control unit wherein said support shelf includes a flat surface with two hooked shaped extensions and a knob and is removably coupled to said spine portion in the same manner as said at least one shelf.

Optionally, the apparatus further comprises a locking bushing mechanism for removably attaching said spine portion to said base stand.

The aforementioned and other embodiments of the present specification shall be described in greater depth in the drawings and detailed description provided below.

BRIEF DESCRIPTION OF THE DRAWINGS

These and other features and advantages of the present specification will be appreciated, as they become better understood by reference to the following detailed description when considered in connection with the accompanying drawings, wherein:

FIG. 1A shows a back view of a monitor stand, in accordance with an embodiment of the present specification;

FIG. 1B shows a front view of a monitor stand, in accordance with an embodiment of the present specification;

FIG. 2B illustrates another view of a monitor arm assembly, in accordance with an embodiment of the present specification;

FIG. 2C illustrates the monitor arm assembly with a magnified view of a first raised portion, in accordance with an embodiment of the present specification;

FIG. 2D illustrates a further magnified view of a first raised portion, in accordance with an embodiment of the present specification;

FIG. 2F illustrates a front view of the monitor arm assembly, in accordance with an embodiment of the present specification;

FIG. 4D illustrates a monitor stand in a partially dismantled configuration showing handles provided for changing the height of the monitor stand, in accordance with an embodiment of the present specification;

FIG. 4E illustrates a magnified view of the handles shown in FIG. 4D, in accordance with an embodiment of the present specification;

FIG. 5A illustrates a collapsible monitor stand cart comprising a plurality of shelves, in accordance with an embodiment of the present specification;

FIG. 5B illustrates the collapsible monitor stand cart with at least one shelf removed in accordance with an embodiment of the present specification;

FIG. 5C illustrates the collapsible monitor stand cart in a dismantled state, in accordance with an embodiment of the present specification;

FIG. 6A illustrates a front view of a shelf attached to a spine portion of the collapsible monitor stand cart in accordance with an embodiment of the present specification;

FIG. 6B illustrates a magnified cross-sectional view of the section A-A marked on FIG. 6A;

FIG. 6C illustrates a magnified view of the portion marked B on FIG. 6B;

FIG. 7A illustrates another front view of a shelf attached to a spine portion of the collapsible monitor stand cart, in accordance with an embodiment of the present specification;

FIG. 7B illustrates a magnified cross-sectional view of the section A-A marked on FIG. 7A;

FIG. 7C illustrates a magnified view of the portion marked B on FIG. 7B;

FIG. 8A illustrates a front view of a spine portion of the monitor stand attached to a base stand, in accordance with an embodiment of the present specification;

FIG. 8B is a magnified cross-sectional view of the portion labeled C-C in FIG. 8A; and FIG. 8C is a magnified view of the portion labeled D in FIG. 8B.

DETAILED DESCRIPTION

Figure 2A:
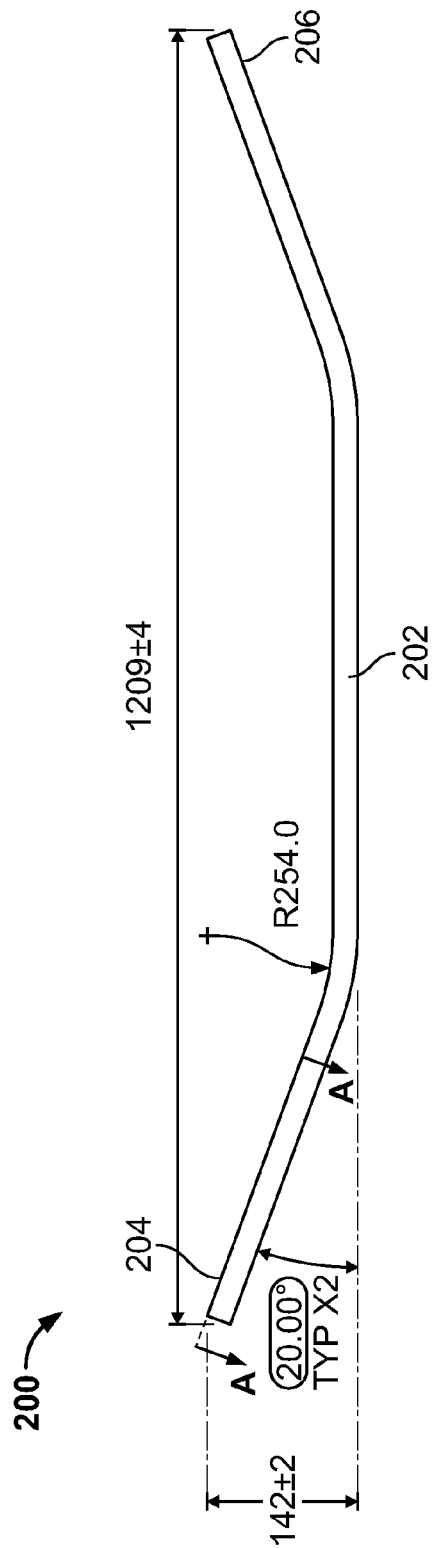
FIG. 2A illustrates a monitor arm assembly, in accordance with an embodiment of the present specification.

The present specification provides a monitor stand for mounting at least one, and up to three monitors. The monitor stand comprises an erect stand coupled with a monitor arm assembly, for supporting one or more monitor screens (or displays), which may be rotated about a top end of the erect portion of the monitor stand. In an embodiment, a backside of a monitor or display is coupled with the monitor arm assembly via a coupling means as described below. In various embodiments, the monitor stand of the present specification may be folded and/or dismantled for transport.

In another embodiment, the present specification provides an integrated cart and monitor stand that comprises at least a spine portion, a base stand attached to a lower end of the spine portion, and multiple shelves for holding equipment related to endoscopes such as a main control unit, additional monitor screens, supplies, etc., along with their respective cords, attached at a plurality of locations along the length of the spine portion. In various embodiments, the base stand and shelves may be dismounted from the spine portion easily without the use of any specialized tools. Further, the weight and dimension of the various parts of the cart and monitor stand facilitate transportation of the same in a mid-sized vehicle.

The present specification is directed towards multiple embodiments. The following disclosure is provided in order to enable a person having ordinary skill in the art to practice the invention. Language used in this specification should not be interpreted as a general disavowal of any one specific embodiment or used to limit the claims beyond the meaning of the terms used therein. The general principles defined herein may be applied to other embodiments and applications without departing from the spirit and scope of the invention. Also, the terminology and phraseology used is for the purpose of describing exemplary embodiments and should not be considered limiting. Thus, the present invention is to be accorded the widest scope encompassing numerous alternatives, modifications and equivalents consistent with the principles and features disclosed. For purpose of clarity, details relating to technical material that is known in the technical fields related to the invention have not been described in detail so as not to unnecessarily obscure the present invention.

The present specification provides a monitor stand 100 for mounting up to three monitors at a time. FIG. 1A shows a backside view of the monitor stand 100, in accordance with one embodiment of the present specification. FIG. 1B shows a front view of the monitor stand 100, in accordance with one embodiment of the present specification. Referring to FIGS. 1A and 1B simultaneously, in various embodiments, the monitor stand 100 enables mounting of up to three monitors 102. In an embodiment, the monitors 102 each weigh a maximum of approximately 20 pounds and are approximately 20 inches wide, although it should be understood that any size monitor may be employed with the stands described in the present specification. In various embodiments, the configuration of the monitor stand 100 can be adjusted for use with monitors of different width or weights. As shown in FIGS. 1A and 1B, the monitors 102 are mounted side to side in an arcuate shape, resembling a bow, such that the backs 102b of the monitors 102 are attachable to the monitor stand 100 and form a convex surface and that the screens 102a of the monitors 102 are facing an endoscope operator (not shown) and form a concave surface.

The monitor stand 100 comprises a monitor arm assembly 104 for mounting or holding the monitors 102 in place. The monitor arm assembly 104 is movably attached to a monitor stand frame 106 which holds the monitor stand 100 in an upright position. In an embodiment, the monitor arm assembly 104 is bow shaped and rotatable with respect to the monitor stand frame 106. In an embodiment, the monitor arm assembly 104 is affixed by a clamp attached to a post on the monitor stand frame 106 that operates as the axis of rotation. Further in an embodiment, a handle is provided on the clamp to enable the user to lock the monitor arm assembly 104 in a desired position with respect to the monitor stand frame 106. This adjustable movement enables an operator to make the monitors 102 face a desired direction by rotating the monitor arm assembly 104. In one embodiment, the monitor arm assembly may be rotated through an angle of 360 degrees from either side with respect to a point of attachment with the monitor stand frame 106. In an embodiment, the monitor arm assembly 104 may be rotated through an angle of 45 degrees from either side with respect to a point of attachment with the monitor stand frame 106. In an embodiment, the monitor arm assembly 104 may be rotated through an angle of 30 degrees from either side with respect to a point of attachment with the monitor stand frame 106.

In an embodiment, the monitors are supported by an isolation transformer that minimizes leakage current that may be caused by the monitors. The isolation transformer transfers electrical power from an alternating current (AC) power source to the monitors while isolating said monitors from the power source. This serves to suppress electrical noise between the monitors and protect against electric shock. In an embodiment, the monitor stand frame 106 is attached with an isolation transformer assembly stand 108 for supporting an isolation transformer and also providing a base for balancing the weight of the monitors 102 supported by the monitor arm assembly 104. The isolation transformer assembly stand 108 has a top surface, a bottom surface, a front side and a back side. Further, a groove is provided on the back side for attaching the monitor stand frame 106. In an embodiment, the isolation transformer is attached to a bracket that is assembled with screws onto the monitor stand frame 106.

Further, in various embodiments, isolation transformer assembly stand 108 comprises at least one wheel, and preferably two front wheels 110 and two rear wheels 112, mounted on the bottom surface of the isolation transformer assembly stand 108 for mobility of the monitor stand 100. In the embodiment shown in FIGS. 1A and 1B, two front wheels 110 and two rear wheels 112 are provided on an underside of the isolation transformer assembly stand 108. The front and rear wheels 110, 112 enable the monitor stand 100 to be mobile. The monitor stand 100 may be moved to a desired location even during operation of the monitors 102. In an embodiment, only the rear wheels 112 are provided with a locking mechanism for fixing the position of the monitor stand 100 in a desired location while in another embodiment, both the front and rear wheels 110, 112 are provided with a locking mechanism.

FIG. 2A illustrates the monitor arm assembly 200, in accordance with an embodiment of the present specification. The monitor arm assembly 200 has an arcuate shape having a middle or center portion 202, that is substantially straight, a first end or left portion 204, that is raised relative to the middle portion, and a second end or right portion 206, that is raised relative to the middle portion. In an embodiment, the monitor arm assembly is approximately 1209 mm long and the two end portions 204, 206 are raised, or bent, at an angle of approximately 20 degrees from the plane of the straight portion 202. Also, in an embodiment, the two end portions 204, 206 are raised, or bent, to a height of approximately 142 mm from the plane of the straight portion 202. One monitor is supported by each of the first end portion 204, the second end portion 206 and the middle straight portion 202.

FIG. 2B illustrates another view of the monitor arm assembly 200. Three monitors may be mounted on the monitor arm assembly 200. In an embodiment, one monitor may be mounted on the first end or left portion 204 by means of a left bracket 208, a second monitor may be mounted on the straight or center portion 202 by means of a center bracket 210 and a third monitor may be mounted on the second end or right portion 206 by means of right bracket 212. The brackets 208, 210 and 212 fix the monitors onto the monitor arm assembly 200 in such a way that the edges of all the monitors are aligned with each other. In various embodiments, the brackets 208, 210, 212 are positioned proximate a center of each corresponding portion 204, 202, 206. The brackets 208, 210, 212 are horizontally slidable and fixable along said center of each portion 204, 202, 206, as described in further detail with respect to slot 214 of FIGS. 2C and 2D. Horizontal movement of the brackets 208, 210, 212 proximate the center of each portion 204, 202, 206 allows for edge-to-edge alignment of monitors of varying sizes. When a left monitor is attached to the left bracket 208, which is affixed to the left portion 204, a right edge of said left monitor is flush with a left edge of an attached center monitor, said center monitoring being attached to the center bracket 210, which, in turn, is affixed to the center portion 202. In the same manner, when a right monitor is attached to the right bracket 212, which is affixed to the right portion 206, a left edge of said right monitor is flush with a right edge of the attached center monitor.

FIG. 2C illustrates the monitor arm assembly 200 with a magnified view of the first end portion 204. FIG. 2D illustrates a further magnified view of the first or left end portion 204. In various embodiments, the monitor arm assembly has a height dimension $h_a$ of approximately 2 inches and a width dimension $w_a$ of approximately 1 inch. As shown in FIGS. 2C and 2D, the end portion 204 comprise a slot 214. The left bracket 208 comprises a protruding pin 216 which is inserted into the slot 214, as shown, and is used for securely attaching the bracket 208 to the first end portion 204 by means of screw 218. In various embodiments, a height dimension $h_s$ of the slot 214 varies from 5.0 millimeters to 10.0 millimeters and, in one embodiment, is preferably 8.2 millimeters, thereby allowing an M8 stud of the bracket 208 to slide into the slot 214 with ease. In various embodiments, a left edge of the slot 214 varies from approximately 120.0 millimeters to 140.0 millimeters and, in one embodiment, is preferably 130.9 millimeters, from a left end of the left end portion 204. In various embodiments, a length dimension $l_s$ of the slot 214 varies from 25.0 millimeters to 50.0 millimeters and, in one embodiment, is preferably 38.2 millimeters, to allow for sliding and positioning of the bracket 208 along the length of the slot 214. This feature enables the monitor arm assembly 200 to accommodate monitors of varying sizes while still allowing for flush edge-to-edge positioning of the monitors, thereby providing a substantially seamless panoramic view of the monitor screens. Right bracket 212 is securely attached to the second or right end portion 206 in a similar manner. In an embodiment, bracket 210 comprises two portions, namely a smaller bracket fixed to the monitor and a bigger bracket attached to the straight portion 202. Both the smaller and the bigger bracket have the same shape/angle on a side rib for better guidance and the bigger bracket comprises a thumb screw that locks the smaller bracket to the straight portion 202.

Figure 2E:
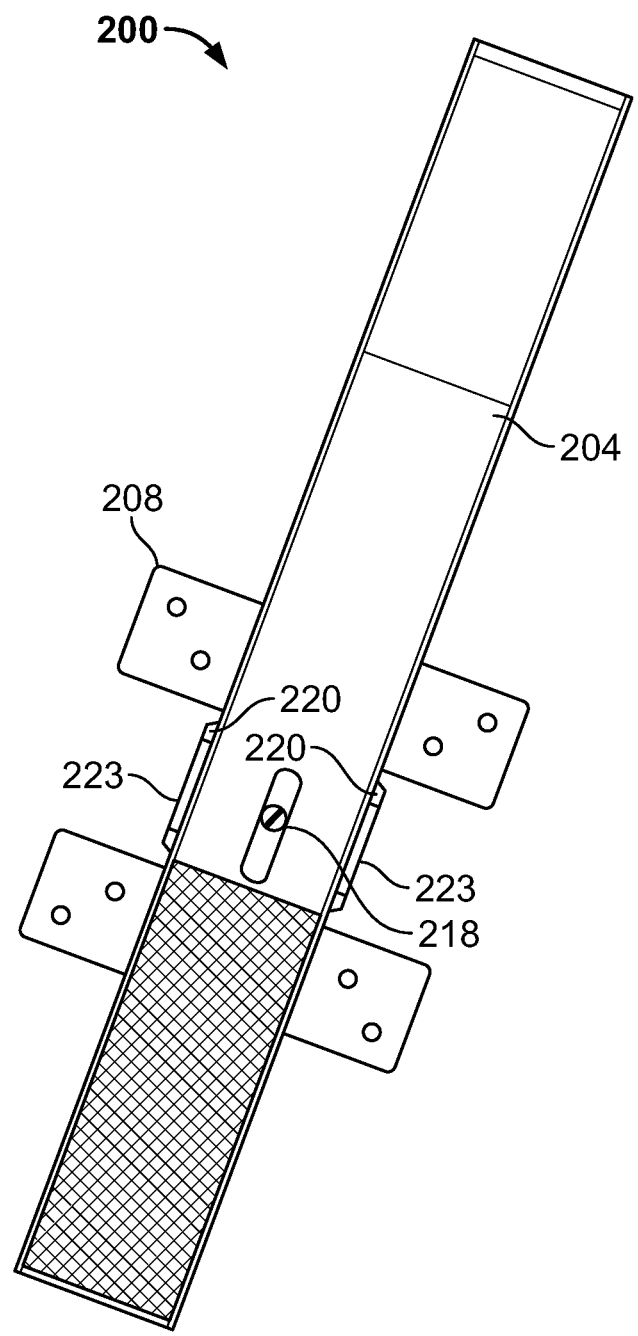
FIG. 2E illustrates a magnified view of a left portion of the monitor arm assembly attached with a left bracket for coupling with a monitor, in accordance with an embodiment of the present specification.

FIG. 2E illustrates a magnified view of a left portion 204 of the monitor arm assembly 200 attached with a left bracket 208 for coupling with a monitor, in accordance with an embodiment of the present specification. As shown, screw 218 holds the bracket 208 in place. Mating areas 220 eliminate rotation of the monitor with respect to the monitor arm assembly 200 and fix the monitor in position. In an embodiment, flanges 223 of the bracket 208 which are parallel to the monitor arm assembly 200 eliminate rotation of a monitor held by the monitor arm assembly 200 and fixes its position. The flanges 223 extend over top and bottom edges of the monitor arm assembly 200 and prevent rotational movement of the bracket 208 about said monitor arm assembly 200. Minimal clearance between the flanges 223 of the bracket 208 and the monitor arm assembly 200 prevents the bracket 208 from rotating, as upon rotation the flanges 223 would hit the monitor arm assembly 200 stopping the rotation.

FIG. 2F illustrates a front view of the monitor arm assembly 200, in accordance with an embodiment of the present specification. The straight or center portion 202 comprises six aluminum spacers 222, 224, 226, 228, 230, 232, and two inserts 234 flush with a front surface of the straight portion 202 of the monitor arm assembly 200. In an embodiment, the distance between the two inserts 234 is 35 mm. Also in an embodiment, a first distance between spacers 222 and 232 is approximately 214.20 mm, a second distance between spacers 224 and 230 is approximately 134.20 mm, and a third distance between spacers 226 and 228 is 88.90 mm. In an embodiment, each of the spacers has an internal diameter of approximately 5/16 inches and a length of approximately one inch. In an embodiment, the spacers are welded flush to the surface of the monitor arm assembly. Referring to FIGS. 1A, 1B, and 2F simultaneously, in various embodiments, the inserts 234 are used to attach the monitor stand frame 106 to the monitor arm assembly 200 in a pivot like arrangement, enabling rotation of the monitor arm assembly 200 coupled with the monitors in a user desired direction with respect to the monitor stand frame 106. In various embodiments, the monitor arm assembly is made of aluminum and has a low weight. The spacers 222, 224, 226, 228, 230, 232 strengthen the structure of the monitor arm assembly. Further in various embodiments, the monitor arm assembly is a hollow structure, and hence, tightening a screw through the structure would cause the screw to bend the assembly internally. Therefore, the use of spacers 222, 224, 226, 228, 230, 232 ensures secure attachment of the monitor arm assembly with the monitor stand frame 106 without causing any damage to the monitor arm assembly.

Figure 2G:
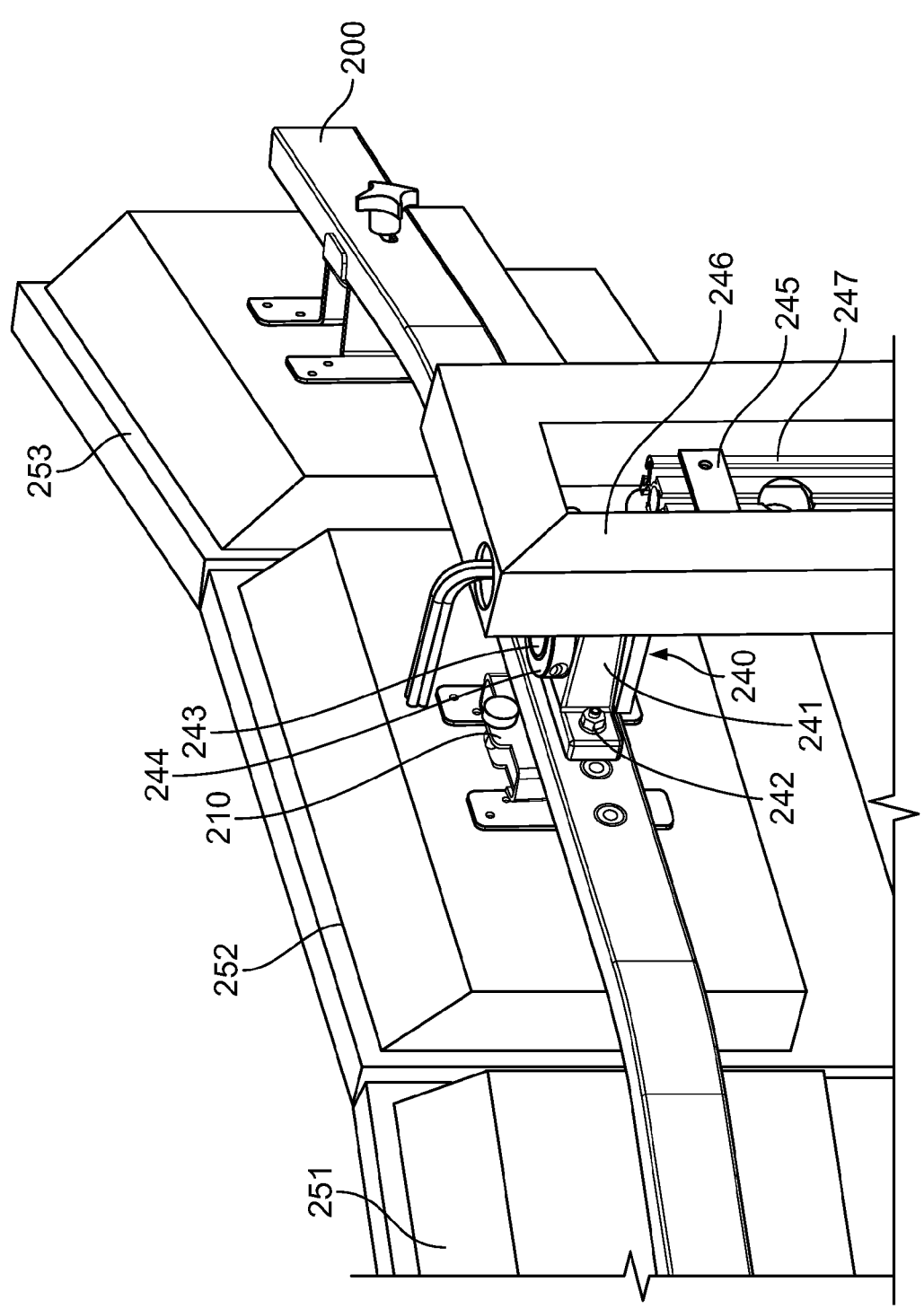
FIG. 2G illustrates a magnified view of a monitor arm assembly with monitors attached thereto coupled to a monitor stand frame, in accordance with one embodiment of the present specification.

FIG. 2G illustrates a magnified view of a monitor arm assembly 200 with monitors 251, 252, 253 attached thereto coupled to a monitor stand frame 246, in accordance with one embodiment of the present specification. A center monitor 252 is attached to the monitor arm assembly 200 via a center mounting bracket 210. The center mounting bracket 210 also serves to couple the monitor arm assembly 200 to a pivoting mechanism 240 of the rigid monitor stand frame 246. The pivoting mechanism comprises a pivoting bearing 241 which is coupled, via a pair of nuts and bolts 242, to the center mounting bracket 210. The bolts pass from the center mounting bracket 210 through the inserts (234 of FIG. 2F) of the monitor arm assembly 200 and are fixed to the pivoting bearing 241 by the nuts, thereby securely attaching the monitor arm assembly 200 to the pivoting assembly 240. The pivoting assembly 240 also includes a pivoting post 243 which is attached via a pivoting mechanism bracket 245 to a center frame portion 247 of the monitor stand frame 246. The center frame portion 247 extends from a top end of the monitor stand 246 to a bottom end of the monitor frame stand 246. The pivoting bearing 241 is positioned on and rotatable about the pivoting post 243. A locking ring 244 attaches to the pivoting post 243 above the pivoting bearing 241 to prevent the pivoting bearing 241, and attached monitor arm assembly 200, from slipping off the pivoting post 243. Once the pivoting mechanism 240 has been assembled, a user may pivot the monitor arm assembly 200 in a horizontal plane relative to the monitor stand frame 246 by applying slight pressure to either side of said monitor arm assembly 200. The pivoting bearing 241 is free to rotate about the pivoting post 243, which allows all three monitors to be pivoted in the same direction/manner concurrently. Additionally, in some embodiments, the pivoting mechanism bracket 245 may be slid vertically along the center frame portion 247 of the monitor stand 246 to adjust the height of the monitor arm assembly 200. In one embodiment, a locking mechanism is included for locking the pivoting mechanism bracket 245 at a fixed vertical position on the center frame portion 247.

In various embodiments, the present specification provides a light weight and compact monitor stand that may be transported in a medium to small size vehicle. Further, in various embodiments, the monitor stand may be dismantled by detaching the monitor stand frame from the isolation transformer base stand and the monitor arm assembly.

Figure 3A:
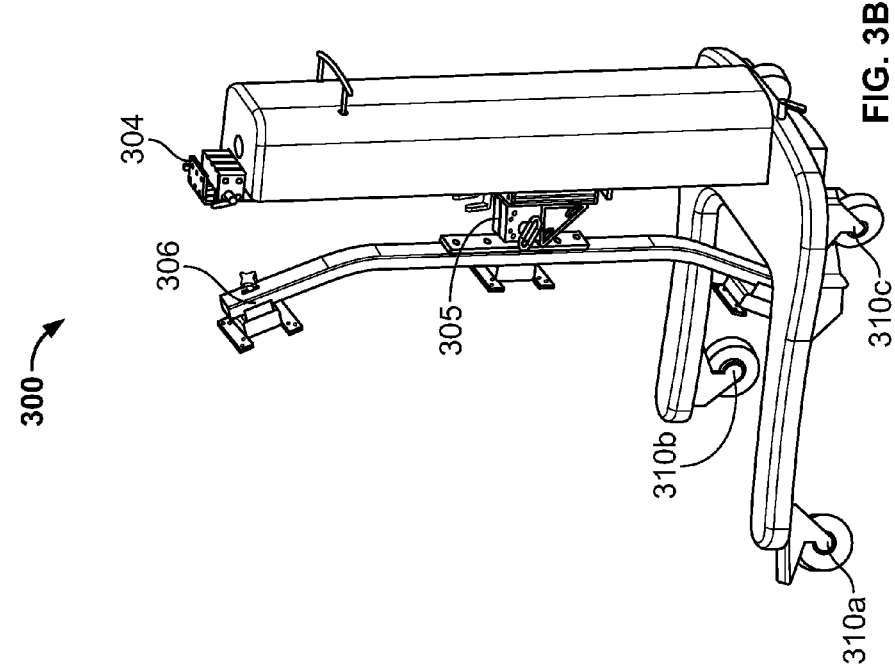
FIG. 3A illustrates an embodiment of the monitor stand that may be folded/dismantled.

In an embodiment, the monitor stand of the present specification may be folded and/or dismantled for transport. FIG. 3A illustrates an embodiment of the monitor stand in an extended and assembled position. The monitor stand 300 comprises a first fixed rigid stand frame or spine portion 302 and a second extendable stand frame portion 304. The second extendable stand frame portion 304 includes a top end and a bottom end and is sized and adapted to telescopically extend from and into the rigid frame portion 302. In various embodiments, the monitor stand 300 includes a locking mechanism for fixing the extendable frame portion 304 at a specific position within and relative to the rigid frame portion 302. In various embodiments, the locking mechanism comprises a lever or button that is pressed by a user, allowing free movement of the extendable frame portion 304. When the lever or button is released, the extendable frame portion 304 becomes locked in place.

Figure 3B:
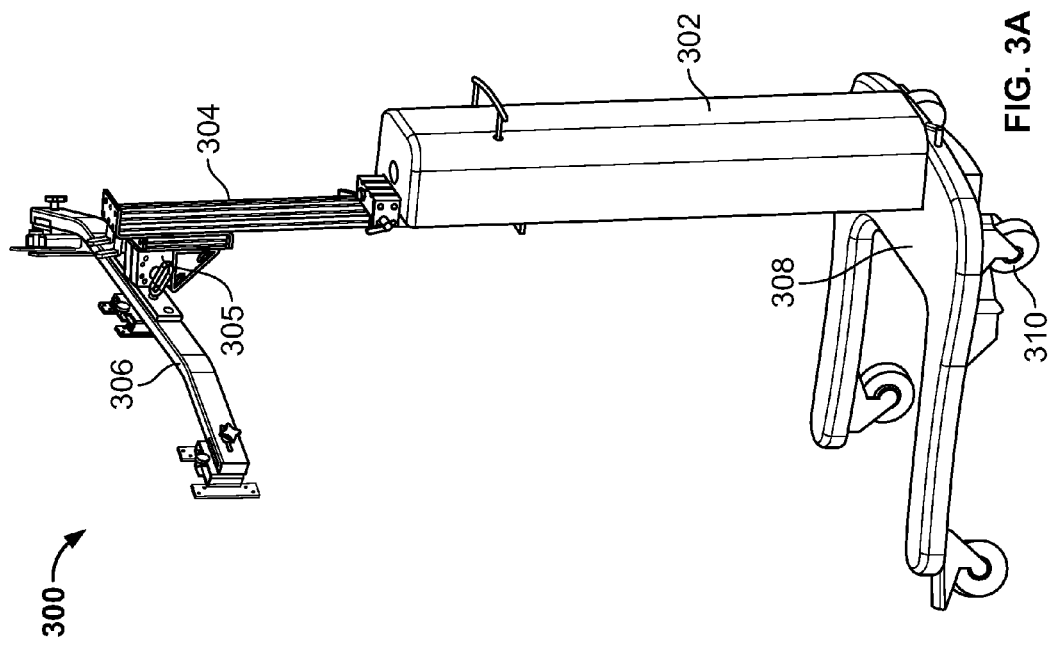
FIG. 3B illustrates the monitor stand partially dismantled, in accordance with an embodiment of the present specification.

A monitor arm assembly 306 is coupled with an upper end of the second extendable stand frame portion 304 via a coupling component 305. The coupling component 305 enhances the collapsibility of the monitor stand 300 in two ways: it allows for detachable coupling of the monitor arm assembly 306 from, and rotation relative to, the second extendable stand frame portion 304; and, it is vertically slidable within said second extendable stand frame portion 304 from a first, top position relative to the second extendable stand frame portion 304, as depicted in FIG. 3A, to a second, bottom position relative to the second extendable stand frame portion 304, as depicted in FIG. 3B, and any position therebetween. The coupling component 305 is further described with reference to FIGS. 4D and 4E.

When in an assembled configuration for supporting one or more monitor screens, the entirety of the monitor arm assembly 306 is horizontal and lies in a plane perpendicular to the plane of the first and second stand frame portions 302, 304, as illustrated. As shown, the second extendable stand frame portion 304 extends from a top end of the first fixed stand frame portion 302. A bottom end of the first fixed stand frame portion 302 is coupled with a base stand 308 provided with wheels 310. In an embodiment, a total height of the monitor stand 300 as illustrated in FIG. 3A in a fully extended position (from a bottom end of the wheels 310 to the top end of the monitor arm assembly 306) is approximately 62.1 inches. It should be noted, however, that the dimensions provided in this specification are provided as exemplary dimensions and that the apparatus of the present specification is not limited to the dimensions provided. The width of the monitor stand 300 measured from an outer end of wheel 310a to an outer end of the wheel 310b is approximately 25.4 inches.

The monitor stand 300 in a dismantled configuration is illustrated in FIG. 3B. When in a stored or disassembled configuration, the entirely of the monitor arm assembly 306 is vertical and lies substantially in the same plane as the first and second stand frame portions 302, 304, as illustrated. The height, measured from a bottom end of the wheels 310c, 310d to a top end of the second extendable stand frame portion 304, is approximately 45.3 inches. Further, in an embodiment, the weight of the spine portion 302, along with the second extendable stand frame portion 304, is approximately 35 pounds; the weight of the monitor arm assembly 306 is approximately 12 pounds; and, the weight of the stand 308 along with wheels 310 is approximately 20 pounds, thus totaling an overall weight of approximately 67 pounds. The low weight of the components of the monitor stand 300 along with its portable size when in a dismantled configuration enables transportation of the monitor stand 300 in a small or medium sized vehicle.

FIG. 3B illustrates the monitor stand 300 partially dismantled, in accordance with an embodiment of the present specification. In an embodiment, in order to dismantle/fold the monitor stand 300, the monitor arm assembly 306 is rotated about the point of connection with the second extendable stand frame portion 304 such that the monitor arm assembly 306 occupies a plane parallel to the plane of the first fixed stand frame portion 302. In an embodiment, the monitor stand 300 includes first and second pins that pass through the coupling component 305 and the monitor arm assembly 306. When the pins are in a first inserted position, the pins fix the position of the monitor arm assembly 306 on the coupling component 305 relative to the second extendable stand frame portion 304. When the pins are in a second removed position, the monitor arm assembly 306 is free to either be detached from the second extendable stand frame portion 304 or to rotate with respect to it. In an embodiment, the monitor stand 300 further includes third and fourth pins that pass through the coupling component 305 and the extendable stand frame portion 304. When the third and fourth pins are in a first inserted position, the vertical position of the coupling component 305 within the extendable stand frame 304 is locked. When the third and fourth pins are in a second removed position, the coupling component 305 may be slid vertically along the extendable frame portion 304. The pins are shown in greater detail with respect to FIGS. 4D and 4E. In addition, the extendable stand frame portion 304 is refracted into the first fixed stand frame portion 302 and the coupling component 305 is slid to its second bottom position to dismantle the monitor stand 300 even further.

Figure 4C:
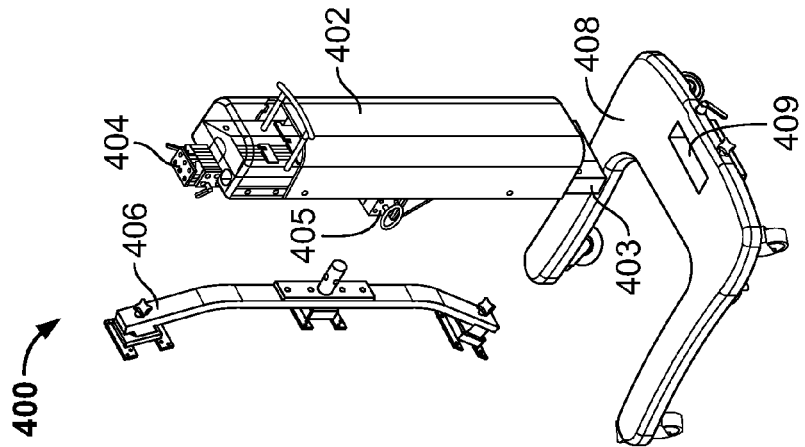
FIG. 4C illustrates the monitor stand in a partially dismantled configuration, in accordance with an embodiment of the present specification.
Figure 4B:
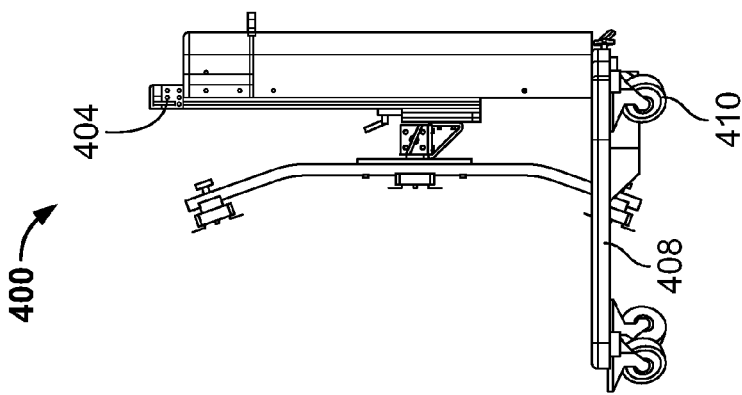
FIG. 4B illustrates the monitor stand in a partially dismantled configuration, in accordance with another embodiment of the present specification.
Figure 4A:
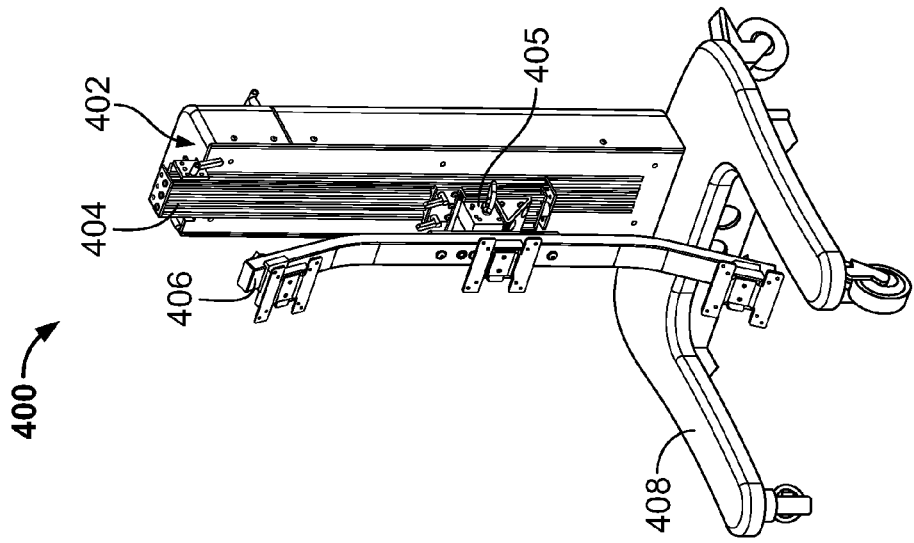
FIG. 4A illustrates the monitor stand in a partially dismantled configuration, in accordance with another embodiment of the present specification.

FIG. 4A illustrates another view of the monitor stand 400 in a dismantled configuration in accordance with an embodiment of the present specification. The height of the monitor stand may be reduced as shown in FIG. 4A as compared to the maximum height that the monitor stand may assume as shown in FIG. 3A. In an embodiment, the height of the monitor stand may be reduced from a maximum height of approximately 62.1 inches to approximately 45.3 inches. FIG. 4A shows the monitor stand comprising the rigid frame portion 402, extendable frame portion 404, coupling component 405, a monitor arm assembly 406, and a base stand 408.

FIG. 4B illustrates a side view of the monitor stand 400 in a partially dismantled configuration, in accordance with an embodiment of the present specification. In an embodiment, the height of the monitor stand as shown measured from a wheel 410 of the base stand 408 to a tip of the extendable frame portion 404 is approximately 45.3 inches.

FIG. 4C illustrates a dismantled view of the monitor stand 400, in accordance with an embodiment of the present specification. As shown, the spine portion, or rigid frame portion 402 is separated from the base stand 408 and the monitor arm assembly 406 is separated from the coupling component 405. Also shown is the extendable frame portion 404. In an embodiment, the rigid frame portion 402 includes an insertion tab 403 at its bottom end for inserting into an opening 409 on the base stand 408 to couple said rigid frame portion 402 with said base stand 408. In an embodiment, the weights of the rigid frame portion 402 with retracted extendable frame portion 404 and coupling component 405, the monitor arm assembly 406, and the base stand 408 are approximately 35 pounds, 12 pounds, and 20 pounds respectively. The weights, as well as the dimensions, of the rigid frame portion 402, the monitor arm assembly 406, and the base stand 408 are such that the monitor stand may be easily transported after dismantling.

After such dismantling, the monitor arm assembly 406, the rigid frame portion 402 with the retracted extendable frame portion 404 and coupling component 405, and the base stand 408 may be packed separately. The dismantled parts may be transported by using a small to medium sized vehicle. In various embodiments, materials such as aluminum, steel and acrylonitrile-butadiene styrene (ABS) are used to manufacture the monitor stand of the present specification. The structure of the monitor stand is designed to withstand vibrations and remain durable.

In various embodiments, four pins are provided that enable the height of the monitor stand to change from that shown in the extended configuration of FIG. 3A to that shown in collapsed configuration of FIG. 4A. In an embodiment, each pin has a screw and nut mechanism that tightens the pin, thereby fixing a position of the coupling component 405 with respect to the extendable frame portion 404 or the monitor arm assembly 406 with respect to the coupling component 405. FIG. 4D illustrates a monitor stand 400 in a dismantled state, in accordance with an embodiment of the present specification. A portion of the monitor stand 412 in FIG. 4D comprises the coupling component 305, pins 414, 416, 418, 4120, and a peg 413 of the monitor arm assembly 406 for attaching the monitor arm assembly 406 to the coupling component 405 and adjusting the position of the coupling component 405 relative to the extendable frame portion 404.

FIG. 4E illustrates a magnified view of the section 412 on FIG. 4D. FIG. 4E shows pins 414, 416, 418 and 420 provided for attaching the monitor arm assembly 406 to the coupling component 405 and for adjusting the position of the coupling component 405 relative to the extendable frame portion 404. Specifically, pins 414, 416 are used for removably attaching the monitor arm assembly 406 to, and rotating it within, the coupling component 405. Pins 418, 420 are used to lock the coupling component 405 in a vertical position relative to the extendable frame portion 404.

With pins 414, 416 removed and the monitor arm assembly 406 dissambled from the monitor stand, a user may couple the monitor arm assembly 406 with the coupling component 405 by inserting peg 413 of the monitor arm assembly 406 into opening 407 of the coupling component 405. At this point, the monitor arm assembly 406 may be freely rotated within the coupling component 405. The peg 413 includes a plurality of openings for receiving pins 414, 416. In an embodiment, the peg 413 is cylindrically shaped and includes four openings or receptacles, each positioned in a same circular plane and 90 degrees apart from one another along an outer surface of the peg 413. The receptacles are configured to receive pins 414, 416. When the monitor arm assembly 406 is rotated such that it is positioned in a vertical plane parallel to the extendable frame portion 404, the two pins 414, 416 can be inserted through a first set of holes in the sides of the coupling component 405 and into two opposing receptacles on the peg 413, fixing the monitor arm assembly 406 in the vertical position for storage and transport. When the monitor arm assembly 406 is rotated such that it is positioned in a horizontal plane perpendicular to the extendable frame portion 404, the two pins 414, 416 can be inserted through holes in the sides of the coupling component 405 and into the other two opposing receptacles on the peg 413, fixing the monitor arm assembly 406 in the horizontal position, ready for the attachment of monitors.

With pins 418, 420 removed, the coupling component 405 is free to move vertically within a channel 411 of the extendable frame portion 404. Inserting pins 418, 420 through a second set of holes in the coupling component 405 and into the extendable frame portion 404 locks the coupling component 405 in a vertical position relative to the extendable frame portion 404. Referring to FIG. 4E, pins 418, 420 are in place and the coupling component 405 is locked in its second, bottom position and is ready for storage and transport.

Figure 4F:
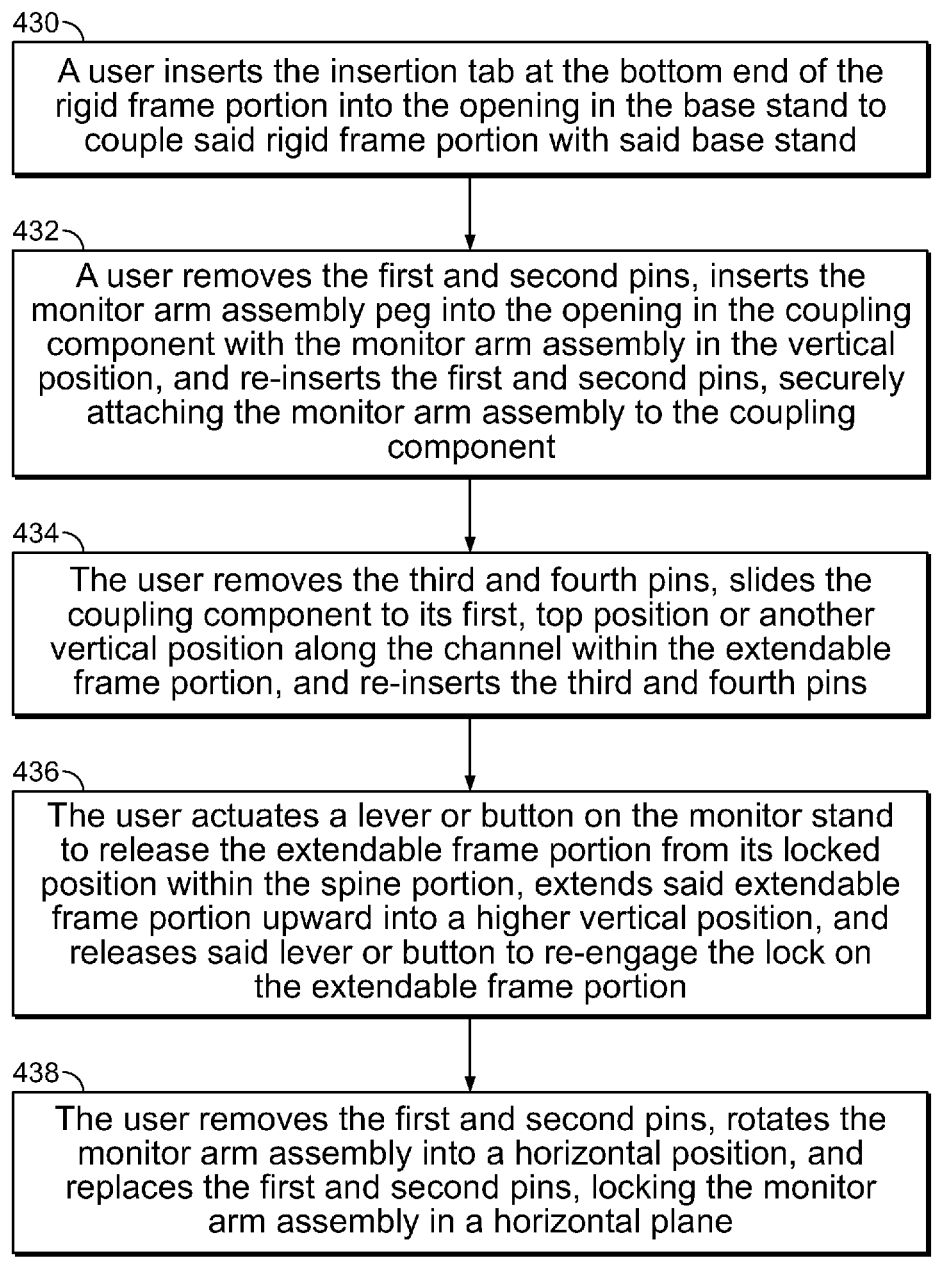
FIG. 4F is a flow chart listing the steps involved in transforming a monitor stand from a stowed configuration, similar to that shown in FIG. 3A, to an operational configuration, similar to that shown in FIG. 3B.

FIG. 4F is a flow chart listing the steps involved in transforming a monitor stand from a stowed configuration, similar to that shown in FIGS. 3B and 4C, to an operational configuration, similar to that shown in FIG. 3A. Optionally, if the rigid frame portion is not attached to the base stand, a user inserts the insertion tab at the bottom end of the rigid frame portion into the opening in the base stand to couple said rigid frame portion with said base stand at step 430. Optionally, if the monitor arm assembly is not attached to the coupling component, a user removes the first and second pins at step 432, inserts the monitor arm assembly peg into the opening in the coupling component with the monitor arm assembly in the vertical position, and re-inserts the first and second pins, securely attaching the monitor arm assembly to the coupling component. At step 434, the user removes the third and fourth pins, slides the coupling component to its first, top position or another vertical position along the channel within the extendable frame portion, and re-inserts the third and fourth pins. Then, at step 436, the user actuates a lever or button on the monitor stand to release the extendable frame portion from its locked position within the spine portion, extends said extendable frame portion upward into a higher vertical position, and releases said lever or button to re-engage the lock on the extendable frame portion. At step 438, the user removes the first and second pins, rotates the monitor arm assembly into a horizontal position, and replaces the first and second pins, locking the monitor arm assembly in a horizontal plane and readying it for monitor attachment. In other embodiments, the step of rotating the monitor arm assembly from the vertical position to the horizontal position may be done prior to extending the height of the coupling component and/or extendable frame portion, as long as care is taken to ensure the monitor arm assembly is high enough to clear the base stand during rotation.

In another embodiment, the present specification provides a collapsible cart and monitor stand that comprises multiple shelves for holding equipment related to endoscopes such as a main control unit, additional monitor screens, etc, along with their respective cords. FIG. 5A illustrates a collapsible cart type monitor stand 500 comprising a stand frame spine portion 502 having a top end and a bottom end, carrying a monitor 504 and provided with shelves 506 for holding equipment such as a main control unit. The stand frame spine portion 502 is coupled at a bottom end to a base stand 508 with wheels 510 for maneuvering the monitor stand 500 from one place to another.

FIG. 5B illustrates the monitor stand 500 with one of the shelves removed. A main control unit 505 is supported by a small support shelf (not shown in the figure). In an embodiment, the dimensions of the support shelf are approximately the same as the dimensions of a base of the main control unit 505 such that the support shelf is not immediately visible when the main control unit 505 is placed on the same.

FIG. 5C illustrates the monitor stand 500 in a dismantled state, in accordance with an embodiment of the present specification. The figure shows the stand frame spine portion 502, shelves 506, base stand 508 with wheels 510 and a monitor support member 512 dismantled and separated. The monitor support member 512 enables connection of a monitor panel with the monitor stand 500. In an embodiment, the components of the fully dismantled monitor stand 500 are configured to fit in a cargo space measuring no greater than 68.9 cubit feet.

Figure 5D:
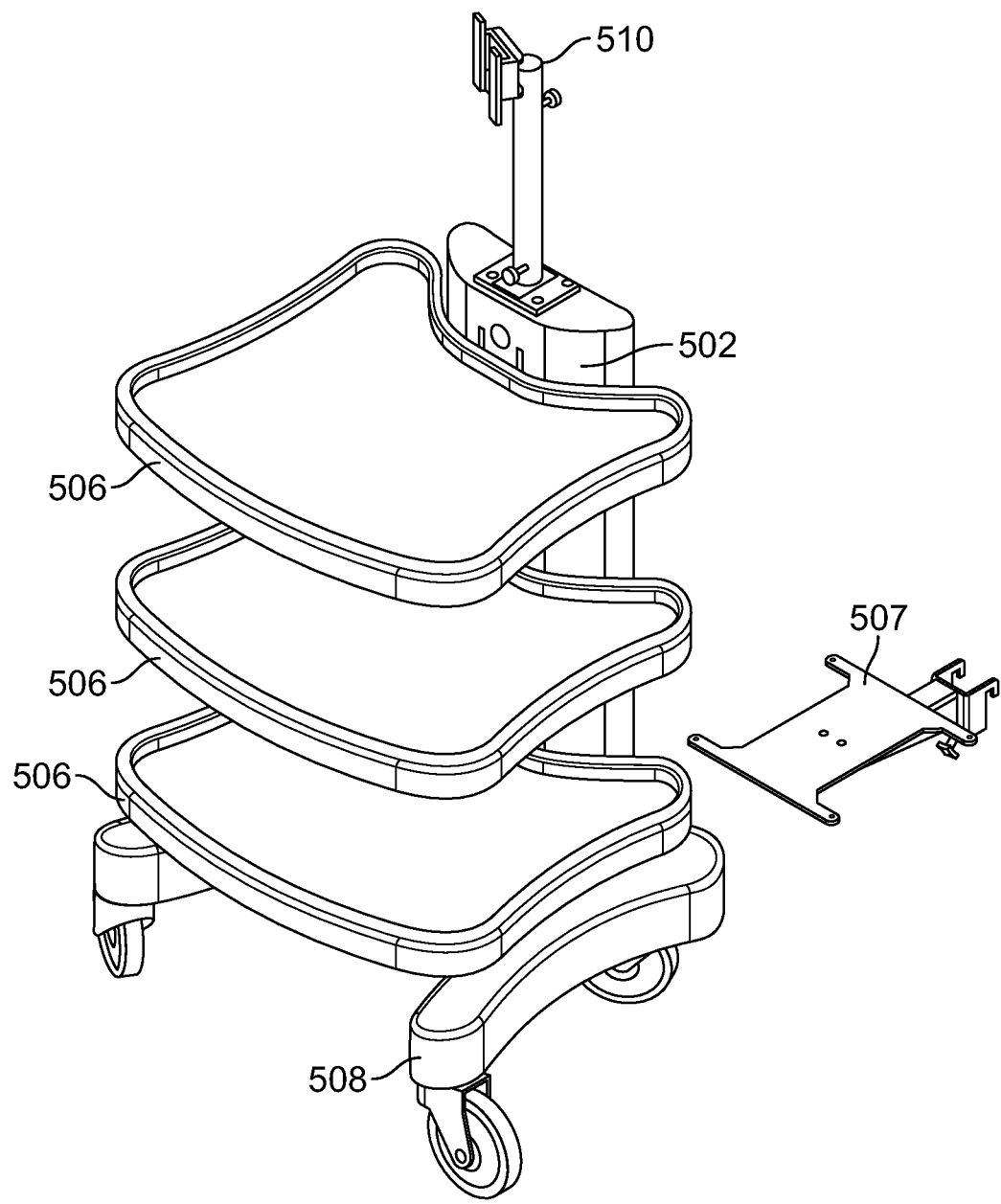
FIG. 5D illustrates another view of the collapsible monitor stand cart, in accordance with an embodiment of the present specification.

FIG. 5D illustrates another view of the monitor stand 500, in accordance with an embodiment of the present specification. A small support shelf 507 is provided to support a main control unit on the monitor stand 500. In various embodiments, similarly to the shelves 506, the support shelf 507 may be attached to the stand frame spine portion 502 at any location along the length of the stand frame spine portion 502. The support shelf 507 may also be easily detached from the stand frame spine portion 502 as explained with reference to FIG. 7. In various embodiments, the support shelf 507 may be used to carry any other equipment.

FIG. 6A illustrates a front view of a shelf 602 attached to a spine portion 604 of the collapsible cart type monitor stand in accordance with an embodiment of the present specification. In various embodiments, a shelf 602 is attached to a spine portion 604 of the monitor stand of the present specification by using brackets and spacers. The shelf 602 may be easily attached to the spine portion 604 without the use of any specialized tools. FIG. 6B illustrates a magnified view of the section A-A 606 marked on FIG. 6A. As shown in FIG. 6B, the shelf 602 comprises a hook shaped extension 608 that fits around a spacer 610 on the spine portion 604. A knob 612 is provided to tighten the shelf 602 on the spine portion 604 in order to fix the position of the shelf 602. FIG. 6C illustrates a magnified view of portion B 614 on FIG. 6B. As shown in FIG. 6C, a linear force 611 applied on the knob 612 (pushing the knob 612 in) is converted by means of a bracket nose surface 616 into torque 613 that is applied in a counter-clockwise direction around the spacer 610, which acts as an axis for rotation of the shelf 602, thereby locking the shelf 602 in a fixed position on the spine portion 604.

FIG. 7A illustrates a front view of a shelf 702 attached to a spine portion 704 of the monitor stand in accordance with an embodiment of the present specification. In various embodiments a shelf 702 is attached to a spine portion 704 of the monitor stand of the present specification by using brackets and spacers. The shelf 702 may be easily detached from the spine portion 704 without the use of any specialized tools. FIG. 7B illustrates a magnified view of the section A-A 706 marked on FIG. 7A. As shown in FIG. 7B, the shelf 702 may be removed from the spine portion 704 by removing a hook shaped extension 708 from around a spacer 710 on the spine portion 704. A knob 712, when pulled out, detaches the shelf 702 from the spine portion 704. FIG. 7C illustrates a magnified view of portion B 714 on FIG. 7B. As shown in FIG. 7C, a linear force 711 applied in an outward direction on the knob 712 releases the knob 712 from the bracket nose surface 716, allowing the shelf 702 to be rotated in a clockwise direction 715 around the spacer 710, thereby loosening the shelf 702 around the spacer 710. The hook shaped extension 708 can then be lifted off the spacer 710 and the shelf 702 can be removed from the cart.

FIG. 8A illustrates a front view of a spine portion 802 of the monitor stand attached to a base stand 804, in accordance with an embodiment of the present specification. In various embodiments, the monitor stand of the present specification comprises a spine portion 802 which may be attached as well as detached easily and quickly from a base stand 804 without the use of any specialized tools. FIG. 8B is a cross-sectional, magnified view of portion C-C 806 in FIG. 8A. FIG. 8C is a magnified view of portion D 808 in FIG. 8B. As shown in FIG. 8C, a locking bushing 810 having a bushing shoulder 812, a locking screw set 814, a thread insert 816, and a knob for tightening 818 are provided in order to enable a quick fastening/release of the base stand 804 from the spine portion 802.

The knob 818 is threaded through a threaded insert 816 which is fixed to the base stand 804. The threaded insert 816 enables the knob 818 to be rotated and moved backward and forward. The knob 818 is then threaded through the bushing 810 until the knob 818 reaches an end of the internal thread of the bushing 810. Next, the bushing 810 and the knob 818 are locked together so that when the knob 818 rotates the bushing 810 rotates as well and moves backward and forward. The bushing 810 and the knob 818 are locked together by the locking screw set 814 inserted through the bushing 810 perpendicular to the knob 818 and touching a flat surface of the knob 818. A user may lock the base stand 804 to the spine portion 802 by pressing the spine portion 802 against a wall of the base stand 804, by rotating the knob 818 in a clockwise direction and moving the bushing 810 forward. The bushing shoulder 812 is used as a hard stop when the spine portion 802 is moved upwards or downwards as the bushing shoulder is located inside holes made in a wall of the spine portion 802.

Hence, the present specification provides a monitor stand comprising at least a spine portion, a base stand and one or more shelves for supporting equipment. The parts of the monitor stand may be assembled easily by a user without the use of any specialized tools. Further, the monitor stand may also be dismantled easily by a user without the use of any specialized tools. The dimensions and weights of the various parts of the monitor stand enable the monitor stand to be quickly dismantled, and transported by using a small to medium sized vehicle.

The above examples are merely illustrative of the many applications of the system of present specification. Although only a few embodiments of the present invention have been described herein, it should be understood that the present invention might be embodied in many other specific forms without departing from the spirit or scope of the invention. Therefore, the present examples and embodiments are to be considered as illustrative and not restrictive.

We claim:

1. An apparatus for supporting one or more monitors, comprising:
   a base stand;
   a first frame portion having a top end and a bottom end coupled with the base stand;
   a second frame portion having a top end, a bottom end, and a channel extending from said top end to said bottom end, said second frame portion telescopically extendable from and into said top of said first frame portion from a first top vertical position to a second bottom vertical position;
   a locking mechanism for fixing said second frame portion in a vertical position within said first frame portion;
   a coupling component vertically slidable within said channel from a third top vertical position to a fourth bottom vertical position; and
   a monitor arm assembly having a center portion, left end portion, right end portion and a peg extending from a rear surface of said center portion wherein a front surface of each of said portions is configured to fixedly receive a monitor, and said peg is configured to insert into said coupling component such that said monitor arm assembly is removably attachable to and rotatable within said coupling component.

2. The apparatus as claimed in claim 1 configured to receive a left monitor, a center monitor, and a right monitor such that a right edge of said left monitor is flush with a left edge of said center monitor and a left edge of said right monitor is flush with a right edge of said center monitor.

3. The apparatus as claimed in claim 1 wherein said left portion and said right portion of said monitor arm assembly each include a slot configured to receive a bracket for attaching a monitor and wherein said bracket is horizontally slidable within said slot for adjusting a horizontal position of an attached monitor.

4. The apparatus as claimed in claim 1 wherein each of said left and right portions are bent at angle of approximately 20 degrees with respect to a horizontal plane of said center portion to create a bow shape.

5. The apparatus as claims in claim 1 wherein said locking mechanism comprises a lever or button which, when actuated, allows said second frame portion to be moved relative to said first frame portion.

6. The apparatus as claimed in claim 1 wherein the base stand is an isolation transformer assembly stand for supporting an isolation transformer, the isolation transformer assembly stand balancing the weight of the monitors coupled with the monitor arm assembly.

7. The apparatus as claimed in claim 6 wherein an underside of the isolation transformer assembly stand is coupled with two front wheels and two rear wheels enabling movement of the assembly stand, further wherein at least the rear wheels comprise a locking mechanism for fixing position of the apparatus.

8. The apparatus as claimed in claim 1 wherein said monitor arm assembly is hollow, composed of aluminium, and includes a plurality of spacers configured to provide structural strength to said monitor arm assembly.

9. The apparatus as claimed in claim 1 wherein said first frame portion is detachable from said base stand.

10. The apparatus as claimed in claim 1 wherein said base stand, first frame portion with second frame portion and coupling component, and said monitor arm assembly have weights of approximately 20 pounds, 35 pounds, and 12 pounds, respectively.

11. The apparatus as claimed in claim 1, wherein said second frame portion is telescopically extendable within said first frame portion to a plurality of vertical positions between said first top vertical position and said second bottom vertical position.

12. The apparatus as claimed in claim 1, wherein said coupling component is vertically slidable within said channel to a plurality of vertical positions between said third top vertical position and said fourth bottom vertical position.

13. The apparatus as claimed in claim 1, transformable from a first collapsed configuration for storage and transport into a second operational configuration for receiving at least one monitor.

14. The apparatus as claimed in claim 13 wherein, when in said first collapsed configuration, said second frame portion is in said second bottom vertical position, said coupling component is in said fourth bottom vertical position, and said monitor arm assembly is removed from said coupling component or rotated within said coupling component such that a long axis of said monitor arm assembly is parallel to said second frame portion.

15. The apparatus as claimed in claim 13 wherein, when in said first collapsed configuration, said apparatus has a height of approximately 45.3 inches.

16. The apparatus as claimed in claim 13 wherein, when in said second operational configuration, said second frame portion is in said first top vertical position or any vertical position above said second bottom vertical position, said coupling component is in said third top vertical position or any vertical position above said fourth bottom vertical position, and said monitor arm assembly is rotated within said coupling component such that a long axis of said monitor arm assembly is perpendicular to said second frame portion.

17. The apparatus as claimed in claim 13 wherein, when in said second operational configuration, said apparatus has a height of approximately 62.1 inches.

18. A method of transforming a monitor stand from a first collapsed configuration into a second operation configuration, said method comprising the steps of:
   providing a monitor stand comprising: a base stand; a first frame portion having a top end and a bottom end coupled with the base stand; a second frame portion having a top end, a bottom end, and a channel extending from said top end to said bottom end, said second frame portion telescopically extendable from and into said top of said first frame portion from a first top vertical position to a second bottom vertical position and a plurality of vertical positions therebetween; a locking mechanism for fixing said second frame portion in a vertical position within said first frame portion; a coupling component vertically slidable within said channel from a third top vertical position to a fourth bottom vertical position and a plurality of vertical positions therebetween; a monitor arm assembly having a center portion, left end portion, right end portion and a peg extending from a rear surface of said center portion wherein a front surface of each of said portions is configured to fixedly receive a monitor, and said peg is configured to insert into said coupling component such that said monitor arm assembly is removably attachable to and rotatable within said coupling component;

sliding the coupling component to the third top position or any other vertical position above said fourth bottom vertical position;

releasing said locking mechanism;

extending said second frame portion from said top end of said first frame portion to said first top vertical position or any other vertical position above said second bottom position;

re-engaging said locking mechanism; and rotating the monitor arm assembly into a horizontal position perpendicular to said second frame portion.

19. The method as claimed in claim 18, wherein, when in said collapsed configuration, said monitor arm assembly is detached from said coupling component, said method further comprising the initial step of:

inserting said peg of said monitor arm assembly into said coupling component with the monitor arm assembly in a vertical position parallel to said second frame portion.

20. The method as claimed in claim 18, wherein, when in said collapsed configuration, said first frame is detached from said base stand, said method further comprising the initial step of coupling said bottom end of said first frame with said base stand.

\* \* \* \* \*